US012622398B2

(12) United States Patent (10) Patent No.: US 12,622,398 B2
Strottman et al. (45) Date of Patent: May 12, 2026

(54) SOYBEAN LINE EC2020188

(71) Applicant: SYNGENTA CROP PROTECTION AG, Basel (CH)

(72) Inventors: Joseph William Strottman, Slater, IA (US); Daniela Sarti Dvorjak, Slater, IA (US)

(73) Assignee: Syngenta Crop Protection AG, Basel (CH)

( * ) Notice: Subject to any disclaimer, the term of this patent is extended or adjusted under 35 U.S.C. 154(b) by 198 days.

(21) Appl. No.: 18/419,828

(22) Filed: Jan. 23, 2024

(65) Prior Publication Data

US 2024/0251738 A1 Aug. 1, 2024

Related U.S. Application Data

(60) Provisional application No. 63/441,501, filed on Jan. 27, 2023.

(51) Int. Cl.
*A01H 5/10* (2018.01)
*A01H 6/54* (2018.01)

(52) U.S. Cl.
CPC ............... *A01H 6/542* (2018.05); *A01H 5/10* (2013.01)

(58) Field of Classification Search
None
See application file for complete search history.

(56) References Cited

U.S. PATENT DOCUMENTS

2021/0251179 A1 * 8/2021 Aponte-Rivera ...... A01H 6/542

OTHER PUBLICATIONS

Ex parte C, 27 U.S.P.Q.2d 1492 (Bd. Pat.App.&Interf.), 1992 WL 515817, Board of Patent Appeals and Interferences (Year: 1992) (Year: 1992).*
Haun et al, The Composition and Origins of Genomic Variation among Individuals of the Soybean Reference Cultivar Williams 82, Plant Physiology, Feb. 2011, vol. 155, pp. 645-655 (Year:2011) (Year: 2011).*
Grobkinsky, Plant phenomics and the need for physiological phenotyping across scales to narrow the genotype-to-phenotype knowledge gap, Journal of Experimental Botany, vol. 66, No. 18, pp. 5429-5440, 2015 (Year: 2015).*
UPOV,Explanatory Notes on Essentially Derived Varieties Under the 1991 Act of the UPOV Convention (Year:2017) (Year: 2017).*
McGowan, Appeal 2019-006060, U.S. Appl. No. 14/996,093 (Year:2020) (Year: 2020).*
USDA, Applying for a Plant Variety Certificate of Protection, www.ams.usda.gov (Year:2023) (Year: 2023).*
Li et al., Identification of ST1 reveals a selection involving hitch-hiking of seed morphology and oil content during soybean domestication, 2022, Plant Biotechnology Journal, vol. 20(6), pp. 1110-1121 (Year: 2022).*

* cited by examiner

*Primary Examiner* — Amjad Abraham
*Assistant Examiner* — Christina L Meadows
(74) *Attorney, Agent, or Firm* — Amanda W. Bublitz

(57) ABSTRACT

The present invention is directed in part to soybean variety EC2020188 breeding and development. The present invention particularly relates to soybean variety EC2020188 and its seed, cells, germplasm, plant parts, and progeny, and methods of using EC2020188, e.g., in a breeding program.

20 Claims, No Drawings

SOYBEAN LINE EC2020188

CROSS-REFERENCE TO RELATED APPLICATIONS

This application claims priority to U.S. Provisional Application No. 63/441,501, filed Jan. 27, 2023, the contents of which are incorporated herein by reference.

THE FIELD OF THE INVENTION

The present invention is in the field of soybean cultivar breeding and development. The present invention particularly relates to the soybean cultivar EC2020142, EC2020188, EC2020491, EC2140213, EC2021110, EC2121951, EC2122916, and/or EC2141386 and its seed, cells, germplasm, plant parts, and progeny, and its use in a breeding program.

BACKGROUND OF THE INVENTION

Soybean *Glycine max* (L) is an important oil seed crop and a valuable field crop. However, it began as a wild plant. This plant and a number of other plants have been developed into valuable agricultural crops through years of breeding and development. The pace of the development of soybeans, into an animal foodstuff and as an oil seed has dramatically increased in the last one hundred years. Planned programs of soybean breeding have increased the growth, yield and environmental hardiness of the soybean germplasm.

Due to the sexual reproduction traits of the soybean, the plant is basically self-pollinating. A self-pollinating plant permits pollen from one flower to be transferred to the same or another flower of the same plant. Cross-pollination occurs when the flower is pollinated with pollen from a different plant; however, soybean cross-pollination is a rare occurrence in nature.

Thus the growth and development of new soybean germplasm requires intervention by the breeder into the pollination of the soybean. The breeders' methods of intervening depends on the type of trait that is being bred. Soybeans are developed for a number of different types of traits including morphology (form and structure), phenotypic characteristics, and for traits like growth, day length, relative maturity, temperature requirements, initiation date of floral or reproductive development, fatty acid content, insect resistance, disease resistance, nematode resistance, fungal resistance, herbicide resistance, tolerance to various environmental factors like drought, heat, wet, cold, wind, adverse soil condition and also for yield. The genetic complexity of the trait often drives the selection of the breeding method.

Due to the number of genes within each chromosome, millions of genetic combinations exist in the breeders' experimental soybean material. This genetic diversity is so vast that a breeder cannot produce the same two cultivars twice using the exact same starting parental material. Thus, developing a single variety of useful commercial soybean germplasm is highly unpredictable, and requires intensive research and development.

The development of new soybeans comes through breeding techniques, such as: recurrent selection, mass selections, backcrossing, single seed descent and multiple seed procedure. Additionally, marker assisted breeding allows more accurate movement of desired alleles or even specific genes or sections of chromosomes to be moved within the germplasm that the breeder is developing. RFLP, RAPD, AFLP, SSR, SNP, SCAR, and isozymes are some of the forms of markers that can be employed in breeding soybeans or in moving traits into soybean germplasm. Other breeding methods are known and are described in various plant breeding or soybean textbooks.

When a soybean variety is being employed to develop a new soybean variety or an improved variety, the selection methods may include backcrossing, pedigree breeding, recurrent selection, marker assisted selection, modified selection and mass selection or a combination of these methods. The efficiency of the breeding procedure along with the goal of the breeding are the main factors for determining which selection techniques are employed. A breeder continuously evaluates the success of the breeding program and therefore the efficiency of any breeding procedures. The success is usually measured by yield increase, commercial appeal and environmental adaptability of the developed germplasm.

The development of new soybean cultivars most often requires the development of hybrid crosses (some exceptions being initial development of mutants directly through the use of the mutating agent, certain materials introgressed by markers, or transformants made directly through transformation methods) and the selection of progeny. Hybrids can be achieved by manual manipulation of the sexual organs of the soybean or by the use of male sterility systems. Breeders often try to identify true hybrids by a readily identifiable trait or the visual differences between inbred and hybrid material. These heterozygous hybrids are then selected and repeatedly selfed and reselected to form new homozygous soybean lines.

Mass and recurrent selection can be used to improve populations. Several parents are intercrossed and plants are selected based on selected characteristics like superior yield or excellent progeny resistance. Outcrossing to a number of different parents creates fairly heterozygous breeding populations.

Pedigree breeding is commonly used with two parents that possess favorable, complementary traits. The parents are crossed to form a F1 hybrid. The progeny of the F1 hybrid is selected and the best individual F2s are selected; this selection process is repeated in the F3 and F4 generations. The inbreeding is carried forward and at approximately F5-F7 the best lines are selected and tested in the development stage for potential usefulness in a selected geographic area.

In backcross breeding a genetic allele or loci is often transferred into a desirable homozygous recurrent parent. The trait from the donor parent is tracked into the recurrent parent. The resultant plant is bred to be essentially the same as the recurrent parent, with the same physiology and morphological characteristics as the recurrent part, with the new desired allele or loci.

The single-seed descent method involves use of a segregating plant population for harvest of one seed per plant. Each seed sample is planted and the next generation is formed. When the F2 lines are advanced to approximately F6 or so, each plant will be derived from a different F2. The population will decline due to failure of some seeds, so not all F2 plants will be represented in the progeny.

New varieties must be tested thoroughly to compare their development with commercially available soybeans. This testing usually requires at least two years and up to six years of comparisons with other commercial soybeans. Varieties that lack the entire desirable package of traits can be used as parents in new populations for further selection or are simply discarded. The breeding and associated testing process is 8 to 12 years of work prior to development of a new variety. Thousands of varietal lines are produced but only a few lines are selected in each step of the process. Thus, the breeding system is like a funnel with numerous lines and selections in the first few years and fewer and fewer lines in the middle years until one line is selected for the final development testing.

The selected line or variety will be evaluated for its growth, development and yield. These traits of a soybean are a result of the variety's genetic potential interacting with its environment. All varieties have a maximum yield potential that is predetermined by its genetics. This hypothetical potential for yield is only obtained when the environmental conditions are near perfect. Since perfect growth conditions do not exist, field experimentation is necessary to provide the environmental influence and to measure its effect on the development and yield of the soybean. The breeder attempts to select for an elevated soybean yield potential under a number of different environmental conditions.

Selecting for good soybean yield potential in different environmental conditions is a process that requires planning based on the analysis of data in a number of seasons. Identification of the varieties carrying a superior combination of traits, which will give consistent yield potential, is a complex science. The desirable genotypic traits in the variety can often be masked by other plant traits, unusual weather patterns, diseases, and insect damage. One widely employed method of identifying a superior plant with such genotypic traits is to observe its performance relative to commercial and experimental plants in replicated studies. These types of studies give more certainty to the genetic potential and usefulness of the plant across a number of environments.

In summary, the goal of the soybean plant breeder is to produce new and unique soybeans and progeny of the soybeans for farmers' commercial crop production. To accomplish this, the plant breeder painstakingly crosses two or more varieties or germplasm. Then the results of this cross are repeatedly selfed or backcrossed to produce new genetic patterns. Newer avenues for producing new and unique genetic alleles in soybeans include introducing (or creating) mutations or transgenes into the genetic material of the soybean are now in practice in the breeding industry. These genetic alleles can alter pest resistance such as disease resistance, insect resistance, nematode resistance, herbicide resistance, or they can alter the plant's environmental tolerances, or its seeds fatty acid compositions, the amount of oil produced, and/or the amino acid/protein compositions of the soybean plant or its seed.

The traits a breeder selects for when developing new soybeans are driven by the ultimate goal of the end user of the product. Thus, if the goal of the end user is to resist a certain plant disease so overall more yield is achieved, then the breeder drives the introduction of genetic alleles and their selection based on disease resistant levels shown by the plant. On the other hand, if the goal is to produce specific fatty acid composition, with for example a high level of oleic acid and/or a lower level of linolenic acid, then the breeder may drive the selection of genetic alleles/genes based on inclusion of mutations or transgenes that alter the levels of fatty acids in the seed. Reaching this goal may allow for the acceptance of some lesser yield potential or other less desirable agronomic trait.

The new genetic alleles being introduced into soybeans are widening the potential uses and markets for the various products and by-products of the oil from seed plants such as soybean. A major product extracted from soybeans is the oil in the seed. Soybean oil is employed in a number of retail products such as cooking oil, baked goods, margarines and the like. Another useful product is soybean meal, which is a component of many foods and animal feedstuffs.

SUMMARY OF THE INVENTION

One embodiment of the invention relates to seed of a soybean cultivar designated EC2020142, EC2020188, EC2020491, EC2140213, EC2021110, EC2121951, EC2122916, and/or EC2141386. The invention also relates to the plant from the seed designated EC2020142, EC2020188, EC2020491, EC2140213, EC2021110, EC2121951, EC2122916, and/or EC2141386, the plant parts, or a plant cell of the soybean cultivar designated EC2020142, EC2020188, EC2020491, EC2140213, EC2021110, EC2121951, EC2122916, and/or EC2141386. The invention also encompasses a tissue culture of regenerable cells, cells or protoplasts being from a tissue selected from the group consisting of: leaves, pollen, embryos, meristematic cells, roots, root tips, anthers, flowers, ovule, seeds, stems, pods, petals and the cells thereof.

The invention in one aspect covers a soybean plant, or parts thereof, or a cell of the soybean plant, having all of the physiological and morphological characteristics of the soybean variety of the invention.

Another aspect of this invention is the soybean plant seed or derived progeny which contains a transgene which provides herbicide resistance, fungal resistance, insect resistance, resistance to disease, resistance to nematodes, male sterility, or which alters the oil profiles, the fatty acid profiles, the amino acids profiles or other nutritional qualities of the seed.

Another aspect of the current invention is a soybean plant further comprising a single locus conversion. In one embodiment, the soybean plant is defined as comprising the single locus conversion and otherwise capable of expressing all of the morphological and physiological characteristics of soybean variety EC2020142, EC2020188, EC2020491, EC2140213, EC2021110, EC2121951, EC2122916, and/or EC2141386. In particular embodiments of the invention, the single locus conversion may comprise a transgenic gene which has been introduced by genetic transformation into the soybean variety EC2020142, EC2020188, EC2020491, EC2140213, EC2021110, EC2121951, EC2122916, and/or EC2141386 or a progenitor thereof. In still other embodiments of the invention, the single locus conversion may comprise a dominant or recessive allele. The locus conversion may comprise potentially any trait upon the single locus converted plant, including male sterility, herbicide resistance, disease resistance, insect resistance, modified fatty acid metabolism, modified carbohydrate metabolism, abiotic stress tolerance, drought tolerance, stress tolerance, modified nutrient deficiency tolerances, or resistance to bacterial disease, fungal disease, nematode disease, or viral disease. The single locus conversion may comprise phytase, fructosyltransferase, levansucrase, alpha-amylase, invertase, starch branching enzyme, or for example, may encode an antisense of stearyl-ACP desaturase. The locus conversion may confer herbicide tolerance, where the tolerance is conferred to an herbicide selected from the group consisting of glyphosate, glufosinate, acetolactate synthase (ALS) inhibitors, hydroxyphenylpyruvate dioxygenase (HPPD) inhibitors, protoporphyrinogen oxidase (PPO) inhibitors, phytoene desaturase (PDS) inhibitors, photosystem II (PSII) inhibitors, dicamba and 2,4-D. The locus conversion may comprise QTLs which may affect a desired trait.

The locus conversion may also comprise a site-specific recombination site, such as an FRT site, Lox site, and/or other recombination sites for site-specific integration. This includes the introduction of at least one FRT site that may be used in the FLP/FRT system and/or a Lox site that may be used in the Cre/Lox system. For example, see Lyznik et al. (2003) Plant Cell Rep 21:925-932; and WO99/25821, which are hereby incorporated by reference. Other systems that may be used include the Gin recombinase of phage Mu (Maeser et al. (1991) Mol Gen Genet 230:170-176); the Pin recombinase of E. coli (Enomoto et al. (1983) J Bacteriol 156:663-668); and the R/RS system of the pSRI plasmid (Araki et al. (1992) J Mol Biol 182:191-203).

This invention embodies a method of introducing a desired trait, or of single locus conversion, into soybean variety derived from EC2020142, EC2020188, EC2020491, EC2140213, EC2021110, EC2121951, EC2122916, and/or EC2141386, wherein the method comprises: (a) crossing a EC2020142, EC2020188, EC2020491, EC2140213, EC2021110, EC2121951, EC2122916, and/or EC2141386 plant with a plant of another soybean variety that comprises the locus or desired trait to produce F1 progeny plants; (b) selecting one or more F1 progeny plants from step (a) that have the desired trait or locus to produce selected progeny plants; (c) selfing the selected progeny plants of step (b) or crossing the selected progeny plants of step (b) with the EC2020142, EC2020188, EC2020491, EC2140213, EC2021110, EC2121951, EC2122916, and/or EC2141386 plants to produce late generation selected progeny plants; (d) crossing or further selecting for later generation selected progeny plants that have the desired trait or locus and physiological and morphological characteristics of soybean variety EC2020142, EC2020188, EC2020491, EC2140213, EC2021110, EC2121951, EC2122916, and/or EC2141386 to produce selected next later generation progeny plants; and optionally (e) repeating crossing or selection of later generation progeny plants to produce progeny plants that comprise the desired trait or locus and all of the physiological and morphological characteristics of said desired trait and of soybean variety EC2020142, EC2020188, EC2020491, EC2140213, EC2021110, EC2121951, EC2122916, and/or EC2141386 when grown in the same location and in the same environment. The locus or desired trait may confer male sterility, herbicide resistance, disease resistance, insect resistance, modified fatty acid metabolism, modified carbohydrate metabolism, or resistance to bacterial disease, fungal disease or viral disease.

The present invention further provides a method for producing a soybean seed with the steps of crossing at least two parent soybean plants and harvesting the hybrid soybean seed, wherein at least one parent soybean plant is the present invention. Another aspect of the invention provides the hybrid soybean seed and the progeny soybean plant and resultant seed, or parts thereof from the hybrid seed or plant or its progeny, including a plant cell from the hybrid plant or its progeny.

In an additional aspect, the invention covers a method for producing a soybean progeny from the invention by crossing soybean line EC2020142, EC2020188, EC2020491, EC2140213, EC2021110, EC2121951, EC2122916, and/or EC2141386, with a second soybean plant to yield progeny soybean seed and then growing progeny soybean seed to develop a derived soybean line.

Yet another aspect of the invention covers a method for a breeding program using plant breeding techniques which employ the soybean plant EC2020142, EC2020188, EC2020491, EC2140213, EC2021110, EC2121951, EC2122916, and/or EC2141386, as plant breeding material and performing breeding by selection techniques, backcrossing, pedigree breeding, marker enhanced selection, locus conversion, mutation and transformation. A single locus conversion of a site-specific recombination system allows for the integration of multiple desired traits at a known recombination site in the genome.

In an additional aspect, the invention covers a method for producing an inbred soybean plant derived from soybean variety EC2020142, EC2020188, EC2020491, EC2140213, EC2021110, EC2121951, EC2122916, and/or EC2141386 by crossing soybean line EC2020142, EC2020188, EC2020491, EC2140213, EC2021110, EC2121951, EC2122916, and/or EC2141386 with a second soybean plant to yield progeny soybean seed, and then growing a progeny plant and crossing said plant with itself or a second progeny plant to produce a progeny plant of a subsequent generation, and then repeating these steps for further subsequent generations to produce an inbred soybean plant derived from soybean variety EC2020142, EC2020188, EC2020491, EC2140213, EC2021110, EC2121951, EC2122916, and/or EC2141386.

In another aspect, the invention covers the plant produced by the methods described above, or a selfed progeny thereof, wherein the plant or selfed progeny comprises the desired trait, single locus, or loci and otherwise comprises essentially all of the physiological and morphological characteristics of soybean variety EC2020142, EC2020188, EC2020491, EC2140213, EC2021110, EC2121951, EC2122916, and/or EC2141386 when grown in the same location and in the same environment.

DETAILED DESCRIPTION

The Following Data is Used to Describe and Enable the Present Soybean Invention.

| Name | Code | Common Name | Description |
|------|------|-------------|-------------|
| Cyst Nematode Race 14 CN14R | CN14R | CN14R | Greenhouse Cyst Nematode Race 14 1 = R, 3 = MR, 5 = seg, 9 = S |
| Cyst Nematode Race 3 CN3_R | CN3_R | CN3_R | Greenhouse Cyst Nematode Race 3 1 = R, 3 = MR, 5 = seg, 9 = S |
| Dead Leaves | DL__R | DL__R | Dead Leaves Rating (when not sure what cause) |
| Early Plot Appearance | EPA_R | | Early Plot Appearance-emergence, evenness of stand V2-V6 |
| Emergence EMRGR | EMRGR | Emerge | Emergence 1 to 9 (1 = best) |
| Flower Color FL_CR | FL_CR | FL_CR | Flower Color 1 = W = White; 2 = P = Purple; 9 = Seg = Segregating (Mixture of Colors) |

-continued

| Name | Code | Common Name | Description |
|------|------|-------------|-------------|
| Frogeye Leaf Spot | FELSR | FELS | Frogeye Leaf Spot rating 1-9 (1 = best) |
| Grain Yield at harvest moisture | YGHMN | YGHMN | Grain Yield at Harvest Moisture |
| Grain Yield at Std MST | YGSMN | Yield | Grain Yield at Standard Moisture-(Qt/H) |
| Green Lodging GLDGR | GLDGR | GrnLod | Green Lodging Rating R5 to R6 1 = All erect; 5 = 45 degree; 9 = flat |
| Green Stem GS__R | GS__R | GrnStem | Green Stem rating 1-9 (1 = best) |
| Harvest Appearance | HVAPR | HVAPR | Overal Harvest Appearance 1 = best; 5 = average; 9 = Poor |
| Harvest Lodging HLDGR | HLDGR | HrvstLod | Harvest Lodging 1 = All erect; 5 = 45 degree; 9 = flat |
| Hilum Color | HILCT | HILCT | Hilum Color G = Grey; BR = Brown; BF = Buff; BL = Black; IB = Imperfect Black; Y = Yellow; IY = Imperfect Yellow; S = Segregating (Mixture of Colors) |
| Maturity Date (MMDD) | MRTYD | MRTYD | Maturity Date (MMDD)-95% of plants in row shed leaves & pods turned mature color |
| Maturity Days from planting | MRTYN | MatDays | Maturity-Days from planting date |
| Moisture % (Field) MST_P | GMSTP | GMSTP | Moisture % (Field) |
| *Phytophthora* Root Rot | PRR_R | PRR | *Phytophthora* Root Rot Field Tolerance. Rating (1 = best) |
| Plant Branching | PLBRR | Branch | Plant Branching Rating 1 = No branching; 5 = Average; 9 = Profuse |
| Plant Canopy Rating | PLCNR | Canopy | Plant Canopy Rating PLCNR 1 = no branching, 5 = average, 9 = profuse |
| Plant Height (cm) | PLHTN | Height | Plant Height in centimeters |
| Pod Color | PD_CR | PD_CR | Pod Color Rating 1 = T = Tawny; 2 = B = Brown; 9 = Seg = Segregating (Mixture of Colors) |
| PRR GENE RPS_T | RPS_T | RPS_T | *Phytophthora* Root Rot GENE, 1C, 1K, No Gene, etc. |
| Pubescence Color | PB_CR | PB_CR | Pubescence Color Rating 1 = G = Gray; 2 = T = Tawny; 4 = Lt = Ligh Tawny; 9 = Seg = Segregating (Mixture of Colors) |
| Root Knot Incogita | MI_T | MI T | Root Knot Incogita trait. R = resistance; MR = mixed resistance; S = susceptible |
| Root Knot Incognita | MI__R | MI__R | Root Knot Incognita rating (1 = best) |
| SCN Race 14 FI% | CN14P | CN14P | Soybean Cyst Nematode Race 14 Female Index % |
| SCN Race 3 F1% | CN3_P | CN3_P | Soybean Cyst Nematode Race 3 FI% |
| Shattering | STR_R | STS_R | Shattering 1-9 (1 = best) |
| Sulfonylurea Tol. | STS_R | STS_R | Sulfonylurea Tolerance Rating 1-9; 1 = Tolerant 9 = sensitive |
| Yield Test Percentage | TESTP | TESTP | The Mean Yield of the variety, expressed as a percentage of the Mean Yield of all varieties in the trial |
| Variety/Hybrid Number | VHNO | VHNO | A code designating a particular variety |
| Iron Chlorosis | IC_R | | Iron Chlorosis Rating or Calculated from Flash & Recovery Mean 1-9 (1 = best) |
| Iron Chlorosis Yellow Flash Rate | ICFLR | | Iron Chlorosis Yellow Flash Rating 1-9 (1 = best) |
| Iron Chlorosis Recovery | ICR_R | | Iron Chlorosis Recovery Rating 1-9 (1 = best) |
| Radiometry IDC Number | IC_N | | Iron Deficiency Chlorosis Adjusted Radiometry Number Calculated from Max Flast and Recovery Mean |
| Brown Stem Rot | BSR_R | BSR | Brown Stem Rot Rating 1-9 (1 = best) |
| Charcoal Rot | CR_R | | Charcoal Rot Rating 1-9 (1 = best) |
| Powdery Mildew | PM_R | | Powdery Mildew Rating 1-9 (1 = best) |
| Bacterial Pustule | BP_R | | Bacterial Pustule Rating 1-9 (1 = best) |
| Rust | RUSTR | | Rust severity overall rating 1-9, 9 being higher severity |
| Sudden Death Syndrome | SDS_R | | Sudden Death Syndrome Rating 1-9 (1 = best) |
| *Sclerotinia* White Mold | SCL_R | SWM | *Sclerotinia* White Mold Severity Rating 1-9 (1 = best) |
| Target Spot | TSP_R | | Target Spot (*Corynespora cassiicola*) Rating 1-9 (1 = best) |
| Stem Canker (Southern) | DPM_R | | Stem Canker (Southern) Rating 1-9 (1 = best) |
| Stem Canker (South) Tolerance | DPMTR | | Stem Canker (Southern) Tolerance Rating 1-9 (1 = best) |

Trait Definitions

Hypocotyl Length (Hyp_R) A rating of a variety's hypocotyl extension after germination when planted at a 5" depth in sand and maintained in a warm germination environment for 10 days.

Leaf Shape Calculated A calculated trait that divides length by width amongst 5 different leaf samples per replicate, measured in cm. 1=lanceolate; 2=oval; 3=ovate.

Seedling Establishment (EMRGR) A rating of uniform establishment and growth of seedlings. Rating is taken between the V1 and V3 growth stages and is a 1 to 9 rating with 1 being the best stand establishment.

Seed Coat Peroxidase (Perox)—seed protein peroxidase activity is a chemical taxonomic technique to separate cultivars based on the presence or absence of the peroxidase enzyme in the seed coat. Ratings are POS=positive for peroxidase enzyme or NEG=negative for peroxidase enzyme. Ratings may also refer to the activity level of the seed protein peroxidase. 1=low activity; 2=high activity.

Chloride Sensitivity (CLS_T) An "Excluder" accumulates chloride and restricts the chloride in the roots. An "Includer" accumulates chloride throughout the plant. Based on molecular markers for analyzing chloride sensitivity, a chloride excluder carries a susceptible marker allele, and a chloride includer has a resistant allele.

Plant Height (PLHTN) The average measured plant height, in centimeters, of 5 uniform plants per plot, taken just prior to harvest.

Plant Branching (PLBRR) Rating of the number of branches and their relative importance to yield. This rating is taken at growth expressive locations. 1=no branching, 5=average and 9=profuse. Ratings taken just prior to harvest.

Green Lodging (GLDGR) Rating based on the average of plants leaning from vertical at the R5 to R6 growth stage. 1=all are erect, 5=average erectness. 9=all are flat. Rating of one is the best rating.

Harvest Lodging (HLDGR) Rating based on the average of plants leaning from vertical at harvest. Lodging score (1=completely upright, 5=45 degree angle from upright; 9=completely prostrate). Rating one is the best rating and ratings are taken just prior to harvest.

MON89788 The transgenic soybean event MON89788 carries a glyphosate tolerance transgene (U.S. Pat. No. 7,632,985 herein incorporated by reference). This transgene may be introgressed into a soybean variety, such that said variety now carries a glyphosate tolerance transgene.

MON87708 The transgenic soybean event MON87708 carries a transgene which expresses a dicamba mono-oxygenase, which confers tolerance to dicamba-based herbicides. This transgene may be introgressed into a soybean variety, such that said variety now carries a dicamba tolerance transgene.

A5547-127 The transgenic soybean event A5547-127 carries a transgene (U.S. Pat. Nos. 8,017,756 and 8,952,142 herein incorporated by reference) which expresses a phosphinothricin N-acetyltransferase (PAT), conferring tolerance to glufosinate-based herbicides. This transgene may be introgressed into a soybean variety, such that said variety now carries a glufosinate tolerance transgene.

DAS-44406-6 The transgenic soybean event DAS-44406-6 carries a cassette (U.S. Pat. No. 9,540,655 herein incorporated by reference) which expresses an aryloxyalkanoate di-oxygenase 12 (AAD-12) protein, a 5-enolypyruvyl shikimate-3-phosphate synthase enzyme (double mutant version, 2mEPSPS), and a phosphinothricin N-acetyltransferase (PAT) enzyme, conferring tolerance to 2,4-D, glyphosate, and glufosinate-based herbicides, respectively. This transgene may be introgressed into a soybean variety, such that said variety now carries a transgene with tolerance to 2,4-D, glyphosate, and glufosinate.

*Phytophthora* Root Rot (PRR_R) means a *Phytophthora* Root Rot field tolerance rating. Rating is 1-9 with one being the best. The information can also include the listing of the actual resistance gene (RPS_T), for example, Rps gene 1C.

Root Knot Nematode (RKN) Greenhouse screen—45 day screen of roots inoculated with eggs and juveniles. Rating Scale based upon female reproduction index on a susceptible check set determined by number of galls present on the root mass. Rating scale is 1-9 with 1 being best. Species specific ratings: *Arenaria* (MA_R), *Incognita* (MI_R), *Javanica* (MJ_R).

Stem Canker (Southern) (DPM_R) Greenhouse screen to identify vertical (gene) type of resistance. One week old soybean seedlings are inoculated with the stem canker pathogen by opening up a small slit into the hypocotyl and depositing a small drop of the fungal suspension. The inoculated seedlings are then placed into a moisture chamber. When the seedlings of the known checks have collapsed, disease severity rating are given on a 1-9 score. One being the best.

Stem canker (Southern) tolerance (DPMTR) Field nursery. The objective of this test is to evaluate the Field Resistance/Tolerance of soybean lines under field conditions. This is necessary due to the fact that of the four known genes that convey vertical type of resistance to stem canker, one gene (Rdc4 from the variety Dowling), exhibits a 40-50% plant kill (false positive) when screened in the greenhouse using the hypocotyl inoculation technique. Lines that scored a rating of 4-9 in the greenhouse are planted in the field. They are sprayed at least 5 times during their first month of development with a spore suspension containing the stem canker fungus. With the inclusion of very susceptible stem canker checks, we are able to identify horizontal (field resistance/tolerance) resistance in certain lines. Quite often, lines scoring a 9 in the greenhouse, rate a score of 1 in the field due to either having the Rdc4 gene or having good field resistance/tolerance. Disease severity scores are once again given on a 1-9 scale when the plants have reached the R6 growth stage of plant development. One being the best.

Brown Stem Rot (BSR_R) This disease is caused by the fungus *Phialophora gregata*. The disease is a late-season, cool-temperature, soil borne fungus which in appropriate favorable weather can cause up to 30 percent yield losses in soybean fields. BSR_R is an opportunistic field rating. The scale is 1-9. One rating is best.

Sudden Death Syndrome (SDS_R) This disease is caused by slow-growing strains of *Fursarium solani* that produce bluish pigments in the central part of the culture when produced on a PDA culture. The disease appears mainly in the reproductive growth stages (R2-R6) of soybeans. Normal diagnostics are distinctive scattered, intervienal chlorotic spots on the leaves. Yield losses may be total or severe in infected fields. The Sudden Death Syndrome Rating is both a field nursery and an opportunistic field rating. It is based on leaf area affected as defined by the Southern Illinois University method of SDS scoring. The scale used for these tests is 1-9. A one rating is best.

*Sclerotinia* White Mold (SCL_R) This disease is caused by the fungal pathogen *Sclerotinia sclerotium*. The fungus can overwinter in the soil for many years as sclerotia and infect plants in prolonged periods of high humidity or rainfall. Yield losses may be total or severe in infected fields. *Sclerotinia* White Mold (SCL_R) rating is a field rating (1-9 scale) based on the percentage of wilting or dead plants in a plot. A one rating is the best.

Frog Eye Leaf Spot (FELSR) This is caused by the fungal pathogen *Cercospora sojina*. The fungus survives as mycelium in infected seeds and in infested debris. With adequate moisture new leaves become infected as they develop until all the leaves are infected. Yield losses may be up to 15% in severe infected fields. Frog Eye Leaf Spot (FELSR) rating is a field rating (1-9 scale) based on the percentage of leaf area affected. The scale is 1-9 where 1=no leaf symptoms and 9=severe leaf symptoms. One is the best rating. To test varieties for Frog Eye Leaf Spot a disease nursery is artificially inoculated with spores. The ratings are done when the plants have reached the R5-R6 growth stage. Visual calibration is done with leaf photos of different frogeye severity ratings as used by the University of Tennessee and Dr. Melvin Newman, State Plant Pathologist for TN.

Soybean Cyst Nematode (SCN) The Soybean Cyst Nematode *Heterodera glycines*, is a small plant-parasitic roundworm that attacks the roots of soybeans. Soybean Cyst Nematode Ratings are taken from a 30 day greenhouse screen using cyst infested soil. The rating scale is based upon female reproduction index (FI %) on a susceptible check set ((female reproduction on a specific line/female reproduction on Susceptible check)*100) where <10%=R (RESISTANT); >10%-<30%=MR (MODERATELY RESISTANT); >30%-<60%=MS (MODERATELY SUSPECTIBLE); >60%=S (SUSPECTIBLE). The screening races include: 1, 3, 5, 14. Individual ratings CN1_P, CN3_P, CN5_P, and CN14_P refer to the resistance to SCN races 1, 3, 5 and 14 FI % respectively.

Powdery Mildew The name given to a group of diseases caused by several closely related fungi. Their common symptom is a grayish-white, powdery mat visible on the surface of leaves, stems, and flower petals. There are many hosts; and although this disease is not considered fatal, plant damage can occur when the infestation is severe.

Soybean Rust (Rust) Previously known as Asian soybean rust. This disease is caused by the fungus *Phakopsora pachyrhiz*.

Maturity Days from Planting (MRTYN) Plants are considered mature when 95% of the pods have reached their mature color. MRTYN is the number of days calculated from planting date to 95% mature pod color.

Relative Maturity Group (RM) Industry Standard for varieties groups, based on day length or latitude. Long day length (northern areas in the Northern Hemisphere) are classified as (Groups 000,00,0). Mid day lengths variety groups lie in the middle group (Groups I-VI). Very short day lengths variety groups (southern areas in Northern Hemisphere) are classified as (Groups VII, VIII, IX). Within a maturity group are sub-groups. A sub-group is a tenth of a relative maturity group (for example, 1.3 would indicate a group 1 and a subgroup 3). Within narrow comparisons, the difference of a tenth of a relative maturity group equates very roughly to a day difference in maturity at harvest.

Grain Yield at Standard Moisture (YGSMN) The actual grain yield at standard moisture (13%) reported in the unit's bushels/acre.

Shattering (STR_R) The rate of pod dehiscence prior to harvest. Pod dehiscence is the process of beans dropping out of the pods. Advanced varieties are planted in a replicated nursery south of their adapted zone to promote early senescence. Mature plots are allowed to stand in the field to endure heat/cool and especially wet/dry cycles. Rating is based on the differences between varieties of the amount of open pods and soybeans that have fallen on the ground. The rating scale is 1-9 with 1=no shattering and 9=severe shattering. One rating is best.

Yield Test Percentage (TESTP) The mean yield of the subject variety expressed as a percentage of the mean yield of all varieties in the trial.

Plant Parts Means the embryos, anthers, pollen, nodes, roots, root tips, flowers, petals, pistols, seeds, pods, leaves, stems, tissue, tissue cultures, meristematic cells and other cells (but only to the extent the genetic makeup of the cell has both paternal and maternal material) and the like.

Palmitic Acid Means a fatty acid, $C_{15}H_{31}COOH$, occurring in soybean. This is one of the five principal fatty acids of soybean oil.

Linolenic Acid Means an unsaturated fatty acid, $C_{17}H_{29}COOH$, occurring in soybean. This is one of the five principal fatty acids of soybean oil.

Stearic Acid Means a colorless, odorless, waxlike fatty acid, $CH_3 (CH_2)_{16}COOH$, occurring in soybean. This is one of the five principal fatty acids of soybean oil.

Oleic Acid Means an oily liquid fatty acid, $C_{17}H_{33}COOH$, occurring in soybean. This is one of the five principal fatty acids of soybean oil.

Linoleic Acid Means an unsaturated fatty acid, $C_{17}H_{31}COOH$, occurring in soybean. This is one of the five principal fatty acids of soybean oil.

Plant Means the plant, in any of its stages of life including the seed or the embryo, the cotyledon, the plantlet, the immature or the mature plant, the plant parts, plant protoplasts, plant cells of tissue culture from which soybean plants can be regenerated, plant calli, plant clumps, and plant cells (but only to the extent the genetic makeup of the cell has both paternal and maternal material) that are intact in plants or parts of the plants, such as pollen, anther, nodes, roots, flowers, seeds, pods, leaves, stems, petals and the like.

Bud Blight (virus-tobacco ringspot virus): A virus disease of soybeans, symptoms form a curled brown crook out of the terminal bud of plants.

Soybean Mosaic (virus): This soybean virus appears as a yellow vein on infected plants. This virus will show in the veins of developing leaves. Leaves look narrow and have puckered margins. Infection results in less seed formed in odd shaped pods. The virus is vectored by aphids.

Bean Pod Mottle Virus (virus): The bean leaf beetle vectored virus. This virus causes a yellow-green mottling of the leaf particularly in cool weather.

Target Spot (fungus—*Alternaria* sp.): This fungus infects leaves, also shows spots on pods and stems.

Anthracnose (fungus—*Colletotrichum dematium* var. *truncatum*): This fungus infects stems, petioles and pods of almost mature plants.

Brown Leaf Spot (fungus—*Septoria glycines*): Early foliar disease on soybeans in springtime.

Downy Mildew (fungus—*Peronospora manshurica*): Fungus appears on the topside of the leaf. The fungus appears as indefinite yellowish-green areas on the leaf.

Purple Seed Stain (fungus—*Cercospora kikuchii*): This fungus is on the mature soybean seed coat and appears as a pink or light to dark purple discoloration.

Seed Decay and Seedling Diseases (fungi—*Pythium* sp., *Phytophthora* sp., *Rhizoctonia* sp., *Diaporthe* sp.): When damage or pathology causes reduced seed quality, then the soybean seedlings are often predisposed to these disease organisms.

Bacterial Blight (bacterium—*Pseudomonas syringae* pv. *glycinea*): A soybean disease that appears on young soybean plants.

Charcoal Rot (fungus—*Macrophomina phaseolina*): Charcoal rot is a sandy soil, mid-summer soybean disease.

*Rhizobium*—Induced Chlorosis: A chlorosis appearing as light green to white which appears 6-8 weeks during rapid plant growth.

Bacterial Pustule (bacterium—*Xanthomonas campestris* pv. *phaseoli*): This is usually a soybean leaf disease; however, the disease from the leaves may infect pods.

Cotton Root Rot (fungus—*Phymatotrichum omnivorum*): This summertime fungus causes plants to die suddenly.

Pod and Stem Blight (fungus—*Diaporthe phaseolorum* var. *sojae*): The fungus attacks the maturing pod and stem and kills the plant.

Treated Seed means the seed of the present invention with a pesticidal composition. Pesticidal compositions include but are not limited to material that are insecticidal, fungicidal, detrimental to pathogens, or sometimes herbicidal.

Locus converted (conversion), also single locus converted (conversion), refers to seeds, plants, and/or parts thereof developed by backcrossing and/or genetic transformation to introduce a given locus that is transgenic in origin, wherein essentially all of the morphological and physiological characteristics of a variety are recovered in addition to the characteristics of the locus or possibly loci which has been transferred into the variety. The locus can be a native locus, a transgenic locus, or a combination thereof. Plants may also be referred to as coisogenic plants.

Variety or Cultivar refer to a substantially homozygous soybean line and minor modifications thereof that retains the overall genetics of the soybean line including but not limited to a subline, a locus conversion, a mutation, a transgenic, or a somaclonal variant. Variety or cultivar include seeds, plants, plant parts, and/or seed parts of the instant soybean line.

Definitions of Staging of Development

The plant development staging system employed in the testing of this invention divides stages as vegetative (V) and reproductive (R). This system accurately identifies the stages of any soybean plant. However, all plants in a given field will not be in the stage at the same time. Therefore, each specific V or R stage is defined as existing when 50% or more of the plants in the field are in or beyond that stage.

The first two stages of V are designated a VE (emergence) and VC (cotyledon stage). Subdivisions of the V stages are then designated numerically as V1, V2, V3 through V (n). The last V stage is designated as V (n), where (n) represents the number for the last node stage of the specific variety. The (n) will vary with variety and environment. The eight subdivisions of the reproductive stages (R) states are also designated numerically. R1=beginning bloom; R2=full bloom; R3=beginning pod; R4=full pod; R5=beginning seed; R6=full seed; R7=beginning maturity; R8=full maturity.

Soybean Cultivar EC2020142, EC2020188, EC2020491, EC2140213, EC2021110, EC2121951, EC2122916, and EC2141386

The present invention comprises a soybean plant, plant part, plant cell, and seed, characterized by molecular and physiological data obtained from the representative sample of said variety deposited with the American Type Culture Collection. Additionally, the present invention comprises a soybean plant comprising the homozygous alleles of the variety, formed by the combination of the disclosed soybean plant or plant cell with another soybean plant or cell.

This soybean variety in one embodiment carries one or more transgenes, for example, the glyphosate tolerance transgene, a dicamba mono-oxygenase gene, a desaturase gene or other transgenes. In another embodiment of the invention, the soybean does not carry any herbicide resistance traits. In yet another embodiment of the invention, the soybean does not carry any transgenes but may carry alleles for aphid resistance, cyst nematode resistance and/or brown stem rot or the like.

The present invention provides methods and composition relating to plants, seeds and derivatives of the soybean cultivar EC2020142, EC2020188, EC2020491, EC2140213, EC2021110, EC2121951, EC2122916, and/or EC2141386. Soybean cultivar EC2020142, EC2020188, EC2020491, EC2140213, EC2021110, EC2121951, EC2122916, and/or EC2141386 has superior characteristics. The EC2020142, EC2020188, EC2020491, EC2140213, EC2021110, EC2121951, EC2122916, and/or EC2141386 line has been selfed sufficient number of generations to provide a stable and uniform plant variety.

Cultivar EC2020142, EC2020188, EC2020491, EC2140213, EC2021110, EC2121951, EC2122916, and/or EC2141386 shows no variants other than expected due to environment or that normally would occur for almost any characteristic during the course of repeated sexual reproduction. Some of the criteria used to select in various generations include: seed yield, emergence, appearance, disease tolerance, maturity, plant height, and shattering data.

The inventor(s) believe that EC2020142, EC2020188, EC2020491, EC2140213, EC2021110, EC2121951, EC2122916, and/or EC2141386 are similar in relative maturity to the comparison varieties. However, as shown in the tables and as described, EC2020142, EC2020188, EC2020491, EC2140213, EC2021110, EC2121951, EC2122916, and/or EC2141386 differs from these cultivars.

Direct comparisons were made between EC2020142, EC2020188, EC2020491, EC2140213, EC2021110, EC2121951, EC2122916, and/or EC2141386 and the listed non-commercial or commercial varieties. Traits measured may include yield, maturity, lodging, plant height, branching, field emergence, and shatter. The results of the comparison are presented in the following tables. The number of tests in which the varieties were compared is shown with the environments, mean and standard deviation for some traits.

It is well known in the art that, by way of backcrossing, one or more traits or loci may be introduced into a given variety while otherwise retaining essentially all of the traits of that variety. An example of such backcrossing to introduce a trait into a starting variety is described in U.S. Pat. No. 6,140,556, where soybean variety Williams '82 was developed using backcrossing techniques to transfer a locus comprising the Rps1 gene to the variety Williams. Williams '82 is comparable to the recurrent parent variety Williams except for resistance to phytopthora rot. Both Williams '82 and Williams have the same relative maturity, indeterminate stems, and flower, pod, pubescence, and hilum color.

EC2020142, EC2020188, EC2020491, EC2140213, EC2021110, EC2121951, EC2122916, and/or EC2141386, or progeny thereof, can carry genetic engineered recombinant genetic material to give improved traits or qualities to the soybean. For example, but not limited to, EC2020142, EC2020188, EC2020491, EC2140213, EC2021110, EC2121951, EC2122916, and/or EC2141386, or progeny thereof, can carry the glyphosate resistance gene for herbicide resistance as taught in the Monsanto patents (WO92/00377, WO92/04449, U.S. Pat. Nos. 5,188,642 and 5,312,910), or a gene which confers tolerance to dicamba-based herbicides, or the STS mutation for herbicide resistance. Additional traits carried in transgenes or mutations can be transferred into EC2020142, EC2020188, EC2020491, EC2140213, EC2021110, EC2121951, EC2122916, and/or EC2141386, or progeny thereof. Some of these genes include genes that give disease resistance to *sclerotinia* such as the oxalate oxidase (Ox Ox) gene as taught in PCT/FR92/00195 Rhone Polunc and/or an oxalate decarboxylase gene for disease resistance or genes designed to alter the soybean oil within the seed such as desaturase, thioesterase genes (shown in EP0472722, U.S. Pat. No. 5,344,771) or genes designed to alter the soybean's amino acid characteristics. This line can be crossed with another soybean line which carries a gene that acts to provide herbicide resistance or alter the saturated and/or unsaturated fatty acid content of the oil within the seed, or the amino acid profile of the seed. Thus through transformation or backcrossing of the present varieties or progeny thereof with a transgenic line carrying the desired event, the present invention further comprise a new transgenic event that is heritable. Some of the available soybean transgenic events include 11-234-01p Dow Soybean 2, 4-D, Glyphosate and Glufosinate Tolerant/DAS-444Ø6-6; 11-202-01p Monsanto Soybean Increased Yield/MON 87712; 10-188-01p Monsanto Soybean Dicamba Tolerant/MON 87708; 09-015-01p BASF Soybean Imadazolinone Tolerant/BPS-CV127-9; 09-328-01p Bayer Soybean Glyphosate and Isoxaflutole Tolerant/FG72; 09-201-01p Monsanto Soybean Improved Fatty Acid Profile/MON 87705; 09-183-01p Monsanto Soybean Stearidonic Acid Produced/MON 87769; 09-082-01p Monsanto Soybean Insect Resistant/MON 87701; 06-354-01p Pioneer Soybean High Oleic Acid/Event 305423; 06-271-01p Pioneer Soybean Glyphosate & Acetolactate Synthase Tolerant/DP-356043-5; 06-178-01p Monsanto Soybean Glyphosate Tolerant/MON 89788; 98-238-01p AgrEvo Soybean Phosphinothricin Tolerant/GU262; 97-008-01p Du Pont Soybean High Oleic Acid Oil/G94-1, G94-19, G-168; 96-068-01p AgrEvo Soybean Glufosinate Tolerant/W62, W98, A2704-12, A2704-21, A5547-35; 96-068-01p AgrEvo Soybean Glufosinate Tolerant/W62, W98, A2704-12, A2704-21, A5547-35; 93-258-01p Monsanto Soybean Glyphosate Tolerant/4-30-2.

The present varieties and/or their progeny can also carry herbicide tolerance where the tolerance is conferred to an herbicide selected from the group consisting of glyphosate, glufosinate, acetolactate synthase (ALS) inhibitors, hydroxyphenylpyruvate dioxygenase (HPPD) inhibitors, protoporphyrinogen oxidase (PPO) inhibitors, phytoene desaturase (PDS) inhibitors, photosystem II (PSII) inhibitors, dicamba and 2,4-D.

This invention also is directed to methods for producing a new soybean plant by crossing a first parent plant with a second parent plant wherein the first or second parent plant is EC2020142, EC2020188, EC2020491, EC2140213, EC2021110, EC2121951, EC2122916, and/or EC2141386 or progeny thereof. Additionally, the present varieties and/or their progeny may be used in the variety development process to derive progeny in a breeding population or crossing. Further, both first and second parent plants can be or be derived from the soybean line EC2020142, EC2020188, EC2020491, EC2140213, EC2021110, EC2121951, EC2122916, and/or EC2141386. A variety of breeding methods can be selected depending on the mode of reproduction, the trait, the condition of the germplasm. Thus, any such methods using the EC2020142, EC2020188, EC2020491, EC2140213, EC2021110, EC2121951, EC2122916, and/or EC2141386 are part of this invention: selfing, backcrosses, locus conversion, recurrent selection, mass selection and the like.

The scope of the present invention includes use of marker methods. In addition to phenotypic observations, the genotype of a plant can also be examined. There are many techniques or methods known which are available for the analysis, comparison and characterization of plant's genotype and for understanding the pedigree of the present invention and identifying plants that have the present invention as an ancestor; among these are Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), and Simple Sequence Repeats (SSRs) which are also referred to as Microsatellites.

A genotypic profile of soybean variety EC2020142, EC2020188, EC2020491, EC2140213, EC2021110, EC2121951, EC2122916, and/or EC2141386 can be used to identify a plant comprising variety EC2020142, EC2020188, EC2020491, EC2140213, EC2021110, EC2121951, EC2122916, and/or EC2141386 as a parent, since such plants will comprise the same homozygous alleles as variety EC2020142, EC2020188, EC2020491, EC2140213, EC2021110, EC2121951, EC2122916, and/or EC2141386. Because the soybean variety is essentially homozygous at all relevant loci, most loci should have only one type of allele present. In contrast, a genetic marker profile of an F1 progeny should be the sum of those parents, e.g., if one parent was homozygous for allele X at a particular locus, and the other parent homozygous for allele Y at that locus, then the F1 progeny will be XY (heterozygous) at that locus. Subsequent generations of progeny produced by selection and breeding are expected to be of genotype XX (homozygous), YY (homozygous), or XY (heterozygous) for that locus position. When the F1 plant is selfed or sibbed for successive filial generations, the locus should be either X or Y for that position.

In addition, plants and plant parts substantially benefiting from the use of variety EC2020142, EC2020188, EC2020491, EC2140213, EC2021110, EC2121951, EC2122916, and/or EC2141386 in their development, such as variety EC2020142, EC2020188, EC2020491, EC2140213, EC2021110, EC2121951, EC2122916, and/or EC2141386 comprising a backcross conversion, locus conversion, transgene, or genetic sterility factor, may be identified by having a molecular marker profile with a high percent identity to soybean variety EC2020142, EC2020188, EC2020491, EC2140213, EC2021110, EC2121951, EC2122916, and/or EC2141386. Such a percent identity might be 90%, 91%, 92%, 93%, 94%, 95%, 96%, 97%, 98%, 99%, 99.5% or 99.9% identical to soybean variety EC2020142, EC2020188, EC2020491, EC2140213, EC2021110, EC2121951, EC2122916, and/or EC2141386.

A genotypic profile of variety EC2020142, EC2020188, EC2020491, EC2140213, EC2021110, EC2121951, EC2122916, and/or EC2141386 also can be used to identify essentially derived varieties and other progeny varieties developed from the use of variety EC2020142, EC2020188, EC2020491, EC2140213, EC2021110, EC2121951, EC2122916, and/or EC2141386, as well as cells and other plant parts thereof. Plants of the invention include any plant having at least 90%, 91%, 92%, 93%, 94%, 95%, 96%, 97%, 98%, 99%, 99.5%, or 99.9% of the markers in the genotypic profile, and that retain 90%, 91%, 92%, 93%, 94%, 95%, 96%, 97%, 98%, 99%, 99.5%, or 99.9% of the morphological and physiological characteristics of variety EC2020142, EC2020188, EC2020491, EC2140213, EC2021110, EC2121951, EC2122916, and/or EC2141386 when grown under the same conditions. Such plants may be developed using markers well known in the art. Progeny plants and plant parts produced using variety EC2020142, EC2020188, EC2020491, EC2140213, EC2021110, EC2121951, EC2122916, and/or EC2141386 may be identified, for example, by having a molecular marker profile of at least 25%, 30%, 35%, 40%, 45%, 50%, 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 99.5% genetic contribution from soybean variety EC2020142, EC2020188, EC2020491, EC2140213, EC2021110, EC2121951, EC2122916, and/or EC2141386, as measured by either percent identity or percent similarity. Such progeny may be further characterized as being within a pedigree distance of variety EC2020142, EC2020188, EC2020491, EC2140213, EC2021110, EC2121951, EC2122916, and/or EC2141386, such as within 1, 2, 3, 4, or 5 or less cross pollinations to a soybean plant other than variety EC2020142, EC2020188, EC2020491, EC2140213, EC2021110, EC2121951, EC2122916, and/or EC2141386, or a plant that has variety EC2020142, EC2020188, EC2020491, EC2140213, EC2021110, EC2121951, EC2122916, and/or EC2141386 as a progenitor. Unique molecular profiles may be identified with other molecular tools, such as SNPs and RFLPs.

The present invention also includes methods of isolating nucleic acids from a plant, a plant part, or a seed of the soybean variety of the invention, analyzing said nucleic acids to produce data, and recording said data. In some embodiments, the data may be recorded on a computer readable medium. The data may comprise a nucleic acid sequence, a marker profile, a haplotype, or any combination thereof. In some embodiments, the data may be used for crossing, selection, or advancement decisions in a breeding program.

A backcross conversion, locus conversion, transgene, or genetic sterility factor, may be in an embodiment of the present invention. Markers can be useful in their development, such that the present invention comprising backcross conversion(s), transgene(s), or genetic sterility factor(s), and are identified by having a molecular marker profile with a high percent identity such as 95%, 96%, 97%, 98%, 99%, 99.5% or 99.9% identical to EC2020142, EC2020188, EC2020491, EC2140213, EC2021110, EC2121951, EC2122916, and/or EC2141386.

These embodiments may be detected using measurements by either percent identity or percent similarity to the deposited material. These markers may detect progeny plants identifiable by having a molecular marker profile of at least 25%, 30%, 35%, 40%, 45%, 50%, 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 99.5% genetic contribution from an embodiment of the present soybean varieties EC2020142, EC2020188, EC2020491, EC2140213, EC2021110, EC2121951, EC2122916, and/or EC2141386. Such progeny may be further characterized as being within a pedigree distance of 1, 2, 3, 4 or 5 or more cross-pollinations to a soybean plant other than the present varieties or a plant that has one of the present varieties as a progenitor. Molecular profiles may be identified with SNP, Single Nucleotide Polymorphism, or other tools also.

Traits are average values for all trial locations, across all years in which the data was taken. In addition to the visual traits that are taken, the genetic characteristic of the plant can also be characterised by its genetic marker profile. The profile can interpret or predict the pedigree of the line, the relation to another variety, determine the accuracy of a listed breeding strategy, or invalidate a suggested pedigree. Soybean linkage maps were known by 1999 as evidenced in Cregan et. al, "An Integrated Genetic Linkage Map of the Soybean Genome" Crop Science 39:1464 1490 (1999); and using markers to determine pedigree claims was discussed by Berry et al., in "Assessing Probability of Ancestry Using Simple Sequence Repeat Profiles: Applications to Maize Inbred Lines and Soybean Varieties" Genetics 165:331 342 (2003), each of which are incorporated by reference herein in their entirety. Markers include but are not limited to Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs) which are also referred to as Microsatellites, and Single Nucleotide Polymorphisms (SNPs). There are known sets of public markers that are being examined by ASTA and other industry groups for their applicability in standardizing determinations of what constitutes an essentially derived variety under the US Plant Variety Protection Act. However, these standard markers do not limit the type of marker and marker profile which can be employed in breeding or developing backcross conversions, or in distinguishing varieties or plant parts or plant cells, or verify a progeny pedigree. Primers and PCR protocols for assaying these and other markers are disclosed in the Soybase (sponsored by the USDA Agricultural Research Service and Iowa State University) located at the world wide web at 129.186.26.94/SSR.html.

Additionally, these markers such as SSRs, RFLP's, SNPs, Ests, AFLPs, gene primers, and the like can be developed and employed to identify genetic alleles which have an association with a desired trait, loci or locus. The allele can be used in a marker assisted breeding program to move traits (native, nonnative (from a different species), or transgenes) into the present varieties, or progeny thereof. The value of markers includes allowing the introgression and/or locus conversion of the allele(s)/trait(s) into the desired germplasm with little to no superfluous germplasm being dragged from the allele/trait donor plant into the present varieties or progeny thereof. This results in formation of, for example, cyst nematode resistance, brown stem rot resistance, aphid resistance, *Phytophthora* resistance, IDC resistance, BT genes, male sterility genes, glyphosate tolerance genes, Dicamba tolerance, HPPD tolerance, rust tolerance, Asian Rust tolerance, fungal tolerance, or drought tolerance genes. Additionally, the present varieties or progeny thereof through transgenes, or if a native trait through markers or backcross breeding, can include a polynucleotide encoding phytase, FAD-2, FAD-3, galactinol synthase or a raffinose synthetic enzyme; or a polynucleotide conferring resistance to soybean cyst nematode, brown stem rot, *phytophthora* root rot, or sudden death syndrome or resistance, tolerance to FUNGAL DISEASES such as: *Alternaria* spp., *Agrobacterium rhizogenes, Calonectria crotalariae, Cercospora kikuchii, Cercospora sojina, Choanephora infundibulifera, Colletotrichum* spp., *Corynespora cassiicola, Curtobacte-*

*rium flaccumfaciens, Dactuliochaeta glycines, Diaporthe phaseolorum, Fusarium oxysporum, Macrophomina phaseolina, Microsphaera difusa, Peronospora manshurica, Phakopsora pachyrhizi, Phialophora gregata, Phomopsis phaseolorum, Phyllosticta sojicola, Phytophthora sojae, Pseudomonas syringae, Pythium* spp., *Rhizoctonia solana, Sclerotinia sclerotiorum, Sclerotium rolfsii, Septoria glycines, Sphaceloma glycines, Thielaviopsis basicota*; or tolerance to BACTERIAL and VIRAL DISEASES such as: *Xanthomonas campestres*, Cowpea Chlorotic Mottle Virus (CCMV), Peanut Mottle Virus (PMV), Tobacco Streak Virus (TSV), Bean Yellow Mosaic Virus (BYMV), Black Gram Mottle Virus (BGMV), Cowpea Mild Mottle Virus (CMMV), Cowpea Severe Mosaic Virus (CSMV), Indonesian Soybean Dwarf Virus (ISDV), Mung Bean Yellow Mosaic Virus (MYMV), Peanut Stripe Virus (VPMM), Soybean Chlorotic Mottle Virus, Soybean Crinkle Leaf Virus, Soybean Yellow Vein Virus (SYVV), Tobacco Mosaic Virus (TMV); NEMATODES such as: *Belonolaimus gracilis, Meloidogyne* spp, *Rotylenchulus reniformis, Pratylenchus* spp., *Hoplolaimus sulumbus, Heterodera schachtii.*

Many traits have been identified that are not regularly selected for in the development of a new cultivar. Using materials and methods well known to those persons skilled in the art, traits that are capable of being transferred, to a cultivar of the present invention include, but are not limited to, herbicide tolerance, resistance for bacterial, fungal, or viral disease, nematode resistance, insect resistance, enhanced nutritional quality, such as oil, starch and protein content or quality, improved performance in an industrial process, altered reproductive capability, such as male sterility or male/female fertility, yield stability and yield enhancement. Other traits include the production of commercially valuable enzymes or metabolites within the present invention.

A transgene typically comprises a nucleotide sequence whose expression is responsible or contributes to the trait, under the control of a promoter capable of directing the expression of the nucleotide sequence at the desired time in the desired tissue or part of the plant. Constitutive, tissue-specific or inducible promoters are well known in the art and have different purposes and each could be employed. The transgene(s) may also comprise other regulatory elements such as for example translation enhancers or termination signals. The transgene may be adapted to be transcribed and translated into a protein, or to encode RNA in a sense or antisense orientation such that it is not translated or only partially translated.

Transgenes may be directly introduced into the cultivar using genetic engineering, site specific insertion techniques, and transformation techniques well known in the art or introduced into the cultivar through a process which uses a donor parent which has the transgene(s) already introgressed. This process of introduction of a transgene(s) or native/non-native traits into the cultivar may use the donor parent in a marker assisted trait conversion process, where the trait may be moved for example by backcrossing using the markers for selection of subsequent generations.

The laboratory-based techniques described above, in particular RFLP and SSR, can be used in such backcrosses to identify the progenies having the highest degree of genetic identity with the recurrent parent. This permits one to accelerate the production of soybean cultivars having at least 90%, 95%, 99% genetic, or genetically identical to the recurrent parent, and further comprising the trait(s) introgressed from the donor parent. Such determination of genetic identity can be based on markers used in the laboratory-based techniques described above.

The last backcross generation is then selfed to give pure breeding progeny for the gene(s) being transferred. The resulting plants have essentially all of the morphological and physiological characteristics of a cultivar of the present invention, in addition to the gene trait(s) transferred to the inbred. The exact backcrossing protocol will depend on the trait being altered to determine an appropriate testing protocol. Although backcrossing methods are simplified when the trait being transferred is a dominant allele, a recessive allele may also be transferred. In this instance it may be necessary to introduce a test of the progeny to determine if the desired trait has been successfully transferred.

In general, methods to transform, modify, edit or alter plant endogenous genomic DNA include altering the plant native DNA sequence or a pre-existing transgenic sequence including regulatory elements, coding and non-coding sequences. These methods can be used, for example, to target nucleic acids to pre-engineered target recognition sequences in the genome. Such pre-engineered target sequences may be introduced by genome editing or modification. As an example, a genetically modified plant variety is generated using "custom" or engineered endonucleases such as meganucleases produced to modify plant genomes (see e.g., WO 2009/114321; Gao et al. (2010) Plant Journal 1:176-187). Another site-directed engineering method is through the use of zinc finger domain recognition coupled with the restriction properties of restriction enzyme. See e.g., Umov, et al., (2010) Nat Rev Genet. 11(9):636-46; Shukla, et al., (2009) Nature 459 (7245):437-41. A transcription activator-like (TAL) elfector-DNA modifying enzyme (TALE or TALEN) is also used to engineer changes in plant genome. See e.g., US20110145940, Cermak et al. (2011), Nucleic Acids Res. 39(12) and Boch et al., (2009), Science 326(5959): 1509-12. Site-specific modification of plant genomes can also be performed using the bacterial type II CRISPR (clustered regularly interspaced short palindromic repeats)/Cas (CRISPR-associated) system. See e.g., Belhaj et al., (2013), Plant Methods 9: 39; The Cas9/ guide RNA-based system and Cas12a/guide RNA-based system, for example, allow targeted cleavage of genomic DNA guided by a customizable small noncoding RNA in plants (see e.g., WO 2015026883A1 and WO2016205711A1, each incorporated herein by reference).

The cultivars of the invention can also be used for transformation where exogenous genes are introduced and expressed by the cultivars of the invention. Genetic variants created either through traditional breeding methods using a cultivar of the present invention or through transformation of such cultivar by any of a number of protocols known to those of skill in the art are intended to be within the scope of this invention (see e.g., Trick et al. (1997) Recent Advances in Soybean Transformation, Plant Tissue Culture and Biotechnology, 3:9-26).

Transformation methods are means for integrating new genetic coding sequences (transgenes) into the plant's genome by the incorporation of these sequences into a plant through man's assistance. Many dicots including soybeans can easily be transformed with *Agrobacterium*. Methods of introducing desired recombinant DNA molecule into plant tissue include the direct infection or co-cultivation of plant cells with *Agrobacterium tumefaciens*, Horsch et al., Science, 227:1229 (1985). Descriptions of *Agrobacterium* vector systems and methods are shown in Gruber, et al., "Vectors for Plant Transformation, in Methods in Plant Molecular Biology & Biotechnology" in Glich et al., (Eds.

pp. 89-119, CRC Press, 1993). Transformed plants obtained via protoplast transformation are also intended to be within the scope of this invention. Other transformation methods such as whiskers, aerosol beam, etc. are well known in the art and are within the scope of this invention. The most common method of transformation after the use of *agrobacterium* is referred to as gunning or microprojectile bombardment. This process has small gold-coated particles coated with DNA (including the transgene) shot into the transformable material. Techniques for gunning DNA into cells, tissue, explants, meristems, callus, embryos, and the like are well known in the prior art.

The DNA used for transformation of these plants clearly may be circular, linear, and double or single stranded.

Some of the time the DNA is in the form of a plasmid. The plasmid may contain additional regulatory and/or targeting sequences which assist the expression or targeting of the gene in the plant. The methods of forming plasmids for transformation are known in the art. Plasmid components can include such items as: leader sequences, transit polypeptides, promoters, terminators, genes, introns, marker genes, etc. The structures of the gene orientations can be sense, antisense, partial antisense or partial sense: multiple gene copies can be used.

After the transformation of the plant material is complete, the next step is identifying the cells or material, which has been transformed. In some cases, a screenable marker is employed such as the beta-glucuronidase gene of the uidA locus of *E. coli*. Then, the transformed cells expressing the colored protein are selected for either regeneration or further use. In many cases, a selectable marker identifies the transformed material. The putatively transformed material is exposed to a toxic agent at varying concentrations. The cells not transformed with the selectable marker, which provides resistance to this toxic agent, die. Cells or tissues containing the resistant selectable marker generally proliferate. It has been noted that although selectable markers protect the cells from some of the toxic effects of the herbicide or antibiotic, the cells may still be slightly affected by the toxic agent by having slower growth rates. If the transformed materials are cell lines then these lines are used to regenerate plants. The cells' lines are treated to induce tissue differentiation. Methods of regeneration of plants are well known in the art. General methods of culturing plant tissues are provided for example by Maki et al. "Procedures for Introducing Foreign DNA into Plants" in Methods in Plant Molecular Biology & Biotechnology, Glich et al. (Eds. pp. 67-88 CRC Press, 1993); and by Phillips et al. "Cell-Tissue Culture and In-Vitro Manipulation" in Soybean & Soybean Improvement, 3rd Edition Sprague et al. (Eds. pp. 345-387) American Society of Agronomy Inc. et al. 1988.

The plants from the transformation process or the plants resulting from a cross using a transformed line or the progeny of such plants which carry the transgene are transgenic plants.

The genes responsible for a specific gene trait are generally inherited through the nucleus. Known exceptions are, e.g. the genes for male sterility, some of which are inherited cytoplasmically, but still act as single gene traits. Male sterile soybean germplasm for hybrid soybean production was taught in U.S. Pat. No. 4,648,204. In a preferred embodiment, a transgene to be introgressed into the cultivar EC2020142, EC2020188, EC2020491, EC2140213, EC2021110, EC2121951, EC2122916, and/or EC2141386 is integrated into the nuclear genome of the donor, non-recurrent parent or the transgene is directly transformed into the nuclear genome of cultivar EC2020142, EC2020188, EC2020491, EC2140213, EC2021110, EC2121951, EC2122916, and/or EC2141386. In another embodiment of the invention, a transgene to be introgressed into cultivar EC2020142, EC2020188, EC2020491, EC2140213, EC2021110, EC2121951, EC2122916, and/or EC2141386 is integrated into the plastid genome of the donor, non-recurrent parent or the transgene is directly transformed into the plastid genome of cultivar EC2020142, EC2020188, EC2020491, EC2140213, EC2021110, EC2121951, EC2122916, and/or EC2141386. In a further embodiment of the invention, a plastid transgene comprises a gene that has transcribed from a single promoter, or two or more genes transcribed from a single promoter.

In another embodiment of the invention, DNA sequences native to soybean as well as non-native DNA sequences can be transformed into the soybean cultivar of the invention and used to alter levels of native or non-native proteins. Various promoters, targeting sequences, enhancing sequences, and other DNA sequences can be inserted into the genome for the purpose of altering the expression of proteins. Reduction of the activity of specific genes (also known as gene silencing or gene suppression) is desirable for several aspects of genetic engineering in plants.

Many techniques for gene silencing are well known to one of skill in the art, including but not limited to, knock-outs (such as by insertion of a transposable element such as mu (Vicki Chandler, The Maize Handbook Ch. 118 (Springer-Verlag 1994)); antisense technology (see, e.g., Sheehy et al. (1988) PNAS USA 85:8805-8809; and U.S. Pat. Nos. 5,107,065; 5,453,566; and 5,759,829); co-suppression (e.g., Taylor (1997) Plant Cell 9:1245; Jorgensen (1990) Trends Biotech 8:340-344; Flavell (1994) PNAS USA 91:3490-3496; Finnegan et al. (1994) Bio/Technology 12:883-888; and Neuhuber et al. (1994) Mol Gen Genet 244:230-241); RNA interference (Napoli et al. (1990) Plant Cell 2:279-289; U.S. Pat. No. 5,034,323; Sharp (1999) Genes Dev 13:139-141; Zamore et al. (2000) Cell 101:25-33; and Montgomery et al. (1998) PNAS USA 95:15502-15507); virus-induced gene silencing (Burton et al. (2000) Plant Cell 12:691-705; Baulcombe (1999) Curr Op Plant Biol 2:109-113); target-RNAspecific ribozymes (Flaselolf et al. (1988) Nature 334:585-591); hairpin structures (Smith et al. (2000) Nature 407:319-320; WO99/53050; WO98/53083); microRNA (Aukerman & Sakai (2003) Plant Cell 15:2730-2741); ribozymes (Steinecke et al. (1992) EMBO J 11:1525; Perriman et al. (1993) Antisense Res Dev 3:253); oligonucleotide mediated targeted modification (e.g, WO03/076574 and WO99/25853); Zn-finger targeted molecules (e.g, WO01/52620; WO03/048345; and WOOO/42219); use of exogenously applied RNA (e.g, US20110296556); and other methods or combinations of the above methods known to those of skill in the art.

A non-exclusive list of traits or nucleotide sequences capable of being transferred into cultivar EC2020142, EC2020188, EC2020491, EC2140213, EC2021110, EC2121951, EC2122916, and/or EC2141386, for example by single locus conversion, using material and methods well known to those persons skilled in the art are as follows: genetic factor(s) responsible for resistance to brown stem rot (U.S. Pat. No. 5,689,035) or resistance to cyst nematodes (U.S. Pat. No. 5,491,081); a transgene encoding an insecticidal protein, such as, for example, a crystal protein of *Bacillus thuringiensis* or a vegetative insecticidal protein from *Bacillus cereus*, such as VIP3 (see, for example, Estruch et al. Nat Biotechnol 15:137-41); a herbicide tolerance transgene whose expression renders plants tolerant to the herbicide, for example, expression of an altered acetohydroxyacid synthase (AHAS) enzyme confers upon plants tolerance to various imidazolinone or sulfonamide herbicides (U.S. Pat. No. 4,761,373.) Other traits capable of being transformed into cultivar EC2020142, EC2020188, EC2020491, EC2140213, EC2021110, EC2121951, EC2122916, and/or EC2141386 include, for example, a non-transgenic trait conferring to cultivar EC2020142, EC2020188, EC2020491, EC2140213, EC2021110, EC2121951, EC2122916, and/or EC2141386 tolerance to imidazolinones or sulfonylurea herbicides; a transgene encoding a mutant acetolactate synthase (ALS) that renders plants resistant to inhibition by sulfonylurea herbicides (U.S. Pat. No. 5,013,659); a gene encoding a mutant glutamine synthetase (GS) resistant to inhibition by herbicides that are known to inhibit GS, e.g. phosphinothricin and methionine sulfoximine (U.S. Pat. No. 4,975,374); and a *Streptomyces* bar gene encoding a phosphinothricin acetyl transferase resulting in tolerance to the herbicide phosphinothricin or glufosinate (U.S. Pat. No. 5,489,520.)

Other genes capable of being transferred into the cultivar EC2020142, EC2020188, EC2020491, EC2140213, EC2021110, EC2121951, EC2122916, and/or EC2141386 of the invention include tolerance to inhibition by cyclohexanedione and aryloxyphenoxypropanoic acid herbicides (U.S. Pat. No. 5,162,602), which is conferred by an altered acetyl coenzyme A carboxylase (ACCase); transgenic glyphosate tolerant plants, which tolerance is conferred by an altered 5-enolpyruvyl-3-phosphoshikimate (EPSP) synthase gene; tolerance to a protoporphyrinogen oxidase inhibitor, which is achieved by expression of a tolerant protoporphyrinogen oxidase enzyme in plants (U.S. Pat. No. 5,767,373.) Genes encoding altered protox resistant to a protox inhibitor can also be used in plant cell transformation methods. For example, plants, plant tissue or plant cells transformed with a transgene can also be transformed with a gene encoding an altered protox (See U.S. Pat. No. 6,808,904 incorporated by reference) capable of being expressed by the plant. The thus-transformed cells are transferred to medium containing the protox inhibitor wherein only the transformed cells will survive. Protox inhibitors contemplated to be particularly useful as selective agents are the diphenylethers (e.g. acifluorfen, 5-[2-chloro-4-(trifluoromethyl)phenoxy]-2-nitrobezoic acid; its methyl ester, or oxyfluorfen, 2-chloro-1-(3-ethoxy-4-nitrophenoxy)-4-(trifluorobenzene)), oxidiazoles, (e.g. oxidiazon, 3-[2,4-dichloro-5-(1-methylethoxy)phenyl]-5-(1,1-dimethylethyl)-1,3,4-oxadiazol-2-(3H)-one), cyclic imides (e.g. S-23142, N-(4-chloro-2-fluoro-5-propargyloxyphenyl)-3,4,5,6-tetrahydrophthalimide; chlorophthalim, N-(4-chlorophenyl)-3,4,5,6-tetrahydrophthalimide), phenyl pyrazoles (e.g. TNPP-ethyl, ethyl 2-[1-(2,3,4-trichlorophenyl)-4-nitropyrazolyl-5-oxy]propionate; M&B 39279), pyridine derivatives (e.g. LS 82-556), and phenopylate and its O-phenylpyrrolidino- and piperidinocarbamate analogs and bicyclic triazolones as disclosed in the International patent application WO 92/04827; EP 532146).

The method is applicable to any plant cell capable of being transformed with an altered protox-encoding gene, and can be used with any transgene of interest.

Expression of the transgene and the protox gene can be driven by the same promoter functional on plant cells, or by separate promoters.

Modified inhibitor-resistant protox enzymes of the present invention are resistant to herbicides that inhibit the naturally occurring protox activity. The herbicides that inhibit protox include many different structural classes of molecules (Duke et al., Weed Sci. 39: 465 (1991); Nandihalli et al., Pesticide Biochem. Physiol. 43: 193 (1992); Matringe et al., FEBS Lett. 245: 35 (1989); Yanase and Andoh, Pesticide Biochem. Physiol. 35: 70 (1989)), including the diphenylethers {e.g. acifluorifen, 5-[2-chloro-4-(trifluoromethyl)phenoxy]-2-nitrobezoic acid; its methyl ester; or oxyfluorfen, 2-chloro-1-(3-ethoxy-4-nitrophenoxy)-4-(trifluorobenzene)}, oxidiazoles (e.g. oxidiazon, 3-[2,4-dichloro-5-(1-methylethoxy)phenyl]-5-(1,1-dimethylethyl)-1,3,4-oxadiazol-2-(3H)-one), cyclic imides (e.g. S-23142, N-(4-chloro-2-fluoro-5-propargyloxyphenyl)-3,4,5,6-tetrahydrophthalimide; chlorophthalim, N-(4-chlorophenyl)-3,4,5,6-tetrahydrophthalimide), phenyl pyrazoles (e.g. TNPP-ethyl, ethyl 2-[1-(2,3,4-trichlorophenyl)-4-nitropyrazolyl-5-oxy]propionate; M&B 39279), pyridine derivatives (e.g. LS 82-556), and phenopylate and its O-phenylpyrrolidino- and piperidinocarbamate analogs.

Direct selection may be applied where the trait acts as a dominant trait. An example of a dominant trait is herbicide tolerance. For this selection process, the progeny of the initial cross are sprayed with the herbicide prior to the backcrossing. The spraying eliminates any plant that does not have the desired herbicide tolerance characteristic, and only those plants that have the herbicide tolerance gene are used in the subsequent backcross. This process is then repeated for the additional backcross generations.

In yet another embodiment of the present invention, a transgene transformed or introgressed into cultivar EC2020142, EC2020188, EC2020491, EC2140213, EC2021110, EC2121951, EC2122916, and/or EC2141386, for example as a single locus conversion, comprises a gene conferring tolerance to a herbicide and at least another nucleotide sequence for another trait, such as for example, insect resistance or tolerance to another herbicide. Another gene capable of being transferred into the cultivar EC2020142, EC2020188, EC2020491, EC2140213, EC2021110, EC2121951, EC2122916, and/or EC2141386 of the invention expresses thioredoxin and thioredoxin reductase enzymes for modifying grain digestibility and nutrient availability (U.S. Pat. Appl. No. 20030145347.)

Further reproduction of the cultivar can occur by tissue culture and regeneration. Tissue culture of various tissues of soybeans and regeneration of plants therefrom is well known and widely published. For example, reference may be had to Komatsuda, T. et al., "Genotype X Sucrose Interactions for Somatic Embryogenesis in Soybean," Crop Sci. 31:333-337 (1991); Stephens, P. A. et al., "Agronomic Evaluation of Tissue-Culture-Derived Soybean Plants," Theor. Appl. Genet. (1991) 82:633-635; Komatsuda, T. et al., "Maturation and Germination of Somatic Embryos as Affected by Sucrose and Plant Growth Regulators in Soybeans *Glycine gracilis* Skvortz and *Glycine max* (L.) Merr.," Plant Cell, Tissue and Organ Culture, 28:103-113 (1992); Dhir, S. et al., "Regeneration of Fertile Plants from Protoplasts of Soybean (*Glycine max* L. Merr.): Genotypic Differences in Culture Response," Plant Cell Reports (1992) 11:285-289; Pandey, P. et al., "Plant Regeneration from Leaf and Hypocotyl Explants of *Glycine wightii* (W. and A.) VERDC. var longicauda," Japan J. Breed. 42:1-5 (1992); and Shetty, K., et al., "Stimulation of In Vitro Shoot Organogenesis in *Glycine max* (Merrill.) by Allantoin and Amides," Plant Science 81:(1992) 245-251; as well as U.S. Pat. No. 5,024,944, issued Jun. 18, 1991 to Collins et al. and U.S. Pat. No. 5,008,200, issued Apr. 16, 1991 to Ranch et al. Thus, another aspect of this invention is to provide cells that upon growth and differentiation produce soybean plants having all or essentially all the physiological and morphological characteristics of cultivar EC2020142, EC2020188, EC2020491, EC2140213, EC2021110, EC2121951, EC2122916, and/or EC2141386. The disclosures, publications, and patents that are disclosed herein are all hereby incorporated herein in their entirety by reference.

Sublines of soybean variety EC2020142, EC2020188, EC2020491, EC2140213, EC2021110, EC2121951, EC2122916, and/or EC2141386 may also be developed and are provided. Although soybean variety EC2020142, EC2020188, EC2020491, EC2140213, EC2021110, EC2121951, EC2122916, and/or EC2141386 contains substantially fixed genetics and is phenotypically uniform with no off types expected, there still remains a small proportion of segregating loci either within individuals or within the population as a whole. Sublining provides the ability to select for these loci, which have no apparent morphological or phenotypic effect on the plant characteristics, but may have an effect on overall yield. For example, the methods described in U.S. Pat. Nos. 5,437,697, 7,973,212, and US2011/0258733, and US2011/0283425 (each of which is herein incorporated by reference) may be utilized by a breeder of ordinary skill in the art to identify genetic loci that are associated with yield potential to further purify the variety in order to increase its yield. A breeder of ordinary skill in the art may fix agronomically relevant loci by making them homozygous in order to optimize the performance of the variety. The development of soybean sublines and the use of accelerated yield technology is a plant breeding technique.

The seed of soybean cultivar EC2020142, EC2020188, EC2020491, EC2140213, EC2021110, EC2121951, EC2122916, and/or EC2141386 further comprising one or more specific, single gene traits, the plant produced from the seed, the hybrid soybean plant produced from the crossing of the cultivar with any other soybean plant, hybrid seed, and various parts of the hybrid soybean plant can be utilized for human food, livestock feed, and as a raw material in industry.

Soybean is the world's leading source of vegetable oil and protein meal. The oil extracted from soybeans is used for cooking oil, margarine, and salad dressings. Soybean oil is composed of saturated, monounsaturated and polyunsaturated fatty acids. It has a typical composition of 11% palmitic, 4% stearic, 25% oleic, 50% linoleic and 9% linolenic fatty acid content ("Economic Implications of Modified Soybean Traits Summary Report", Iowa Soybean Promotion Board & American Soybean Association Special Report 92S, May 1990.) Changes in fatty acid composition for improved oxidative stability and nutrition are constantly sought after. (U.S. Pat. No. 5,714,670 Soybeans Having Low Linolenic Acid and Low Palmitic Acid Contents; U.S. Pat. No. 5,763,745 Soybeans Having Low Linolenic Acid Content and Palmitic Acid Content of at Least Eleven Percent; U.S. Pat. No. 5,714,668 Soybeans Having Low Linolenic Acid And Elevated Stearic Acid Content; U.S. Pat. No. 5,714,669 A17 Soybeans Having Low Linolenic Acid Content and Descendents; U.S. Pat. No. 5,710,369 A16 Soybeans Having Low Linolenic Acid Content and Descendents; U.S. Pat. No. 5,534,425 Soybeans Having Low Linolenic Acid Content and Method of Production; U.S. Pat. No. 5,750,844 Soybeans Capable of Forming a Vegetable Oil Having Specified Concentrations of Palmitic and Stearic Acids; U.S. Pat. No. 5,750,845 Soybeans Capable of Forming a Vegetable Oil Having a Low Saturated Fatty Acid Content; U.S. Pat. No. 5,585,535 Soybeans and Soybean Products Having Low Palmitic Acid Content; U.S. Pat. No. 5,850,029 Soybean Designated AX7017-1-3; U.S. Pat. No. 5,663,485 Soybean Designated A89-259098; U.S. Pat. No. 5,684,230 Soybean Designated AX 4663-5-4-5; U.S. Pat.

No. 5,684,231 Soybean Designated A1937 NMU-85; U.S. Pat. No. 5,714,672 Soybean Designated ElginEMS-421; U.S. Pat. No. 5,602,311 Soybeans and Soybean Products Having High Palmitic Acid Content; U.S. Pat. No. 5,795,969 Soybean Vegetable Oil Having Elevated Concentrations of Both Palmitic and Stearic Acid; U.S. Pat. No. 5,557,037 Soybeans Having Elevated Contents of Saturated Fatty Acids; U.S. Pat. No. 5,516,980 Soybean Variety XB37ZA; U.S. Pat. No. 5,530,183 Soybean Variety 9253; U.S. Pat. No. 5,750,846 Elevated Palmitic Acid Production in Soybeans; U.S. Pat. No. 6,060,647 Elevated Palmitic Acid Production in Soybeans; U.S. Pat. No. 6,025,509 Elevated Palmitic Acid Production in Soybeans; U.S. Pat. No. 6,133,509 Reduced Linolenic Acid Production in Soybeans; U.S. Pat. No. 5,986,118 Soybean Vegetable Oil Possessing a Reduced Linolenic Acid Content; U.S. Pat. No. 5,850,030 Reduced Linolenic Acid Production in Soybeans). Industrial uses of soybean oil that is subjected to further processing include ingredients for paints, plastics, fibers, detergents, cosmetics, and lubricants. Soybean oil may be split, inter-esterified, sulfurized, epoxidized, polymerized, ethoxylated, or cleaved. Designing and producing soybean oil derivatives with improved functionality, oliochemistry is a rapidly growing field. The typical mixture of triglycerides is usually split and separated into pure fatty acids, which are then combined with petroleum-derived alcohols or acids, nitrogen, sulfonates, chlorine, or with fatty alcohols derived from fats and oils.

The techniques of seed treatment application are well known to those skilled in the art, and they may be used readily in the context of the present invention. The seed treating compositions can be applied to the seed as slurry, mist or a soak or other means know to those skilled in the art of seed treatment. Seed treatments may also be applied by other methods, e.g., film coating or encapsulation. The coating processes are well known in the art, and employ, for seeds, the techniques of film coating or encapsulation, or for the other multiplication products, the techniques of immersion. Needless to say, the method of application of the compositions to the seed may be varied and is intended to include any technique that is to be used.

The term "fungicide" as utilized herein is intended to cover compounds active against phytopathogenic fungi that may belong to a very wide range of compound classes. Examples of compound classes to which the suitable fungicidally active compound may belong include both room temperature (25.degree. C.) solid and room temperature liquid fungicides such as: triazole derivatives, strobilurins, carbamates (including thio- and dithiocarbamates), benzimidazoles (thiabendazole), N-trihalomethylthio compounds (captan), substituted benzenes, carboxamides, phenylamides and phenylpyrroles, and mixtures thereof.

The present invention includes a method for preventing damage by a pest to a seed of the present invention and/or shoots and foliage of a plant grown from the seed of the present invention. Broadly the method includes treating the seed of the present invention with a pesticide. The pesticide is a composition that stops pests including insects, diseases, and the like. Broadly compositions for seed treatment can include but is not limited to any of one of the following: an insecticide, or a fungicide.

The method comprises treating an unsown seed of the present invention with neonicotinoid composition. One of these compositions is thiamethoxam. Additionally, the neonicotinoid composition can include at least one pyrethrin or synthetic pyrethroid, to reduce pest damage. More specifically there is a method of seed treatment which employs thiamethoxam and at least one pyrethrin or pyrethroid are comprised within a seed coating treated on the seed of the present invention. The combination, if thiamethoxam is employed, can be coated at a rate which is greater than 200 gm/100 kg of seed. The method includes having at least one of the pyrethroids being a systemic insecticide.

The pyrethrin or synthetic pyrethroid, if employed can be selected from the group consisting of taufluvalinate, flumethrin, trans-cyfluthrin, kadethrin, bioresmethrin, tetramethrin, phenothrin, empenthrin, cyphenothrin, prallethrin, imiprothrin, allethrin and bioallethrin.

The fungicidally active compounds and/or the insecticidal active compounds are employed in a fungicidally and/or insecticidally effective amount in the composition. Mixtures of one or more of the following active compounds are usable as an active component treatment of the seed of the present invention. Examples of suitable individual compounds for use in seed treatments are listed below. Where known, the common name is used to designate the individual compounds (q.v. the Pesticide Manual, 12th edition, 2001, British Crop Protection Council).

Suitable triazole derivatives include propiconazole, difenconazole, tebuconazole, tetraconazole and triticonazole. Suitable strobilurins include trifloxystrobin, azoxystrobin, kresoxim-methyl and picoxystrobin. Suitable carbamates include thiram. Suitable substituted benzenes include PCNB and chlorothalonil. Suitable carboxamides include carboxin. Specific phenylamides usable in the compositions and methods include metalaxyl. A specific phenylpyrrole usable in the composition is fludioxonil.

Other suitable fungicidal compounds that maybe mentioned are Benomyl (also known as Benlate), Bitertanol, Carbendazim, Capropamid, Cymoxanil, Cyprodinil, Ethirimol, Fenpiclonil, Fenpropimorph, Fluquinconazole, Flutolanil, Flutriafol, Fosetyl-aluminum, Fuberidazole, Guazatine, Hymexanol, Kasugamycin, Imazalil, Imibenconazole, Iminoctadine-triacetate, Ipconazole, Iprodione, Mancozeb, Maneb, Mepronil, Metalaxyl, Metalaxyl-M (Mefenoxam), Metconazole, Metiram, MON 65500 (Silthiopham-ISO proposed), Myclobutanil, Nuarimol, Oxadixyl, Oxine-copper, Oxolinic acid, Pefurazoate, Pencycuron, Prochloraz, Propamocarb hydrochloride, Pyroquilon, Silthiopham—see MON 65500, Tecnazene, Thifluzamide, Thiophenatemethyl, Tolclofos-methyl, Triadimenol, Triazoxide and Triflumizole.

The fungicidally active compounds and/or the insecticidal active compounds are employed in a fungicidally and/or insecticidally effective amount in the composition. Mixtures of one or more of the following active compounds also are usable as an active component treatment of the seed of the present invention.

In one seed treatment, mixtures of at least one ambient liquid fungicide (for example, a phenylamide such as R-metalaxyl) and at least one ambient solid fungicide (for example, a phenylpyrrole such as fludioxonil) could be employed. The apparatus for providing the appropriate amount of seed treatment of a specific chemical composition for a seed are well known in the seed coating industry (See, for example, U.S. Pat. Nos. 5,632,819 and 5,891,246).

Soybean seeds, plants, and plant parts may be used or processed for food, animal feed, or a raw material(s) for industry. Soybean is not just a seed it is also used as a grain. Soybean is widely used as a source of protein for animal feeds for poultry, swine and cattle. The soybean grain is a commodity. The soybean commodity plant products include but are not limited to protein concentrate, protein isolate, soybean hulls, meal, flower, oil and the whole soybean itself. Soybean seeds can be crushed, or a component of the seeds can be extracted in order to make a plant product, such as protein concentrate, protein isolate, soybean hulls, meal, flour, or oil for a food or feed product. Methods of producing a plant product, such as protein concentrate, protein isolate, soybean hulls, meal, flour, or oil for a food or feed product are provided. Also provided are the protein concentrate, protein isolate, soybean hulls, meal, flour, or oil produced by the methods.

Oil extracted from soybeans is used for cooking oil, margarine, and salad dressings. Soybean oil has a typical composition of 11% palmitic, 4% stearic, 25% oleic, 50% linoleic, and 9% linolenic fatty acid content. Industrial uses of soybean oil, which is typically subjected to further processing, include ingredients for paints, plastics, fibers, detergents, cosmetics, lubricants, and biodiesel fuel. Soybean oil may be split, inter-esterified, sulfurized, epoxidized, polymerized, ethoxylated, or cleaved. To produce oil, the harvested soybeans are cracked, adjusted for moisture content, rolled into flakes, and then the oil is solvent-extracted. The oil extract is refined, optionally blended and/or hydrogenated. Some soybean varieties have modified fatty acid profiles and can be used to produce soybean oil with a modified fatty acid composition. Oil with 3% or less linolenic acid is classified as low linolenic oil, oil with less than 1% linolenic acid is classified as ultra low linolenic oil. Oil with 70% or higher of oleic acid is classified as high oleic oil.

Soybeans are also used as a food source for both animals and humans. Soybeans are widely used as a source of protein for animal feed. The fibrous hull is removed from whole soybean and the oil is extracted. The remaining meal is a combination of carbohydrates and approximately 50% protein. This remaining meal is heat treated under well-established conditions and ground in a hammer mill. Soybean is a predominant source for livestock feed components. In addition to soybean meal, soybean can be used to produce soy flour. Soy flour refers to defatted soybeans where special care was taken during desolventizing to minimize protein denaturation and to retain a high nitrogen solubility index (NSI) in making the flour. Soy flour is the typical starting material for production of soy concentrate and soy protein isolate. Defatted soy flour is obtained from solvent extracted flakes, and contains less than 1% oil. Full-fat soy flour is made from whole beans and contains about 18% to 20% oil. Low-fat soy flour is made by adding back some oil to defatted soy flour. The lipid content varies, but is usually between 4.5-9%. High-fat soy flour can also be produced by adding soybean oil to defatted flour at the level of 15%. Lecithinated soy flour is made by adding soybean lecithin to defatted, low-fat or high-fat soy flours to increase dispersibility and impart emulsifying properties.

For human consumption, soybean can be used to produce edible ingredients which serve as an alternative source of dietary protein. Common examples include milk, cheese, and meat substitutes. Additionally, soybean can be used to produce various types of fillers for meat and poultry products. Vitamins and/or minerals may be added to make soy products nutritionally more equivalent to animal protein sources as the protein quality is already roughly equivalent.

DEPOSIT INFORMATION

Applicants have made a deposit of seeds of soybean line EC2020188 with the American Type Culture Collection (ATCC) Patent Depository, 10801 University Blvd., Manassas, VA 20110. The ATCC number of the deposit is PTA-127457. The date of deposit for PTA-127457 was Dec. 6, 2022, and the seed was tested on Jan. 11, 2023 and found to be viable. Access to this deposit will be available during the pendency of the application to the Commissioner for Patents and persons determined by the Commissioner to be entitled thereto upon request. Upon granting of a patent on any claims in the application, the Applicants will make the deposit available to the public pursuant to 37 CFR § 1.808. Additionally, Applicants will meet the requirements of 37 CFR § 1.801-1.809, including providing an indication of the viability of the sample when the deposit is made. The ATCC deposit will be maintained in that depository, which is a public depository, for a period of 30 years, or 5 years after the last request, or for the enforceable life of the patent, whichever is longer, and will be replaced if it becomes nonviable during that period.

EC2020142 is employed in a number of plot repetitions to establish trait characteristics.

EC2020142 is a novel soybean cultivar designated EC2020142 with high yield potential and tolerance to glyphosate, glufosinate, and 2,4-D herbicides. The invention relates to seeds of the cultivars EC2020142, plants of the cultivars EC2020142 and to methods for producing a soybean plant produced by crossing the soybean EC2020142 by itself or another soybean genotype.

EC2020142 is a Group 1 soybean cultivar. This variety has an RM of 1.000. To be sold commercially in the United States where late group 1 soybeans are grown. Specific areas where best adaptation occurs include Minnesota and South Dakota. The target for this variety is geographic areas that grow Group 1 maturity glyphosate, glufosinate, and 2,4-D tolerant soybean varieties.

The characteristics and traits of EC2020142 are listed below.

TABLE 1

| CHARACTERISTICS AND TRAITS | | | | | |
|---|---|---|---|---|---|
| Herbicide Transgene | | | DAS-44406-6 | | |
| Insect Transgene | | | | | |
| Other Transgene | | | | Relative Maturity | 1.000 |
| Sulfonylurea Tolerance | N | | Seed Shape | Hypocotyl Color | |
| Metribuzin Tolerance | MET_R | | Seed Coat Luster | Plant Morphological | PGTIb |
| Aphid Gene | U | | Peroxidase | Leaf Color | |
| % Protein @ 13% mst | | | Seed Size g/100 seeds | Leaf Shape Calculated | |
| % Oil @13% mst | | | Growth Habit | INDET | Leaf Shape |
| | | | Plant Health | | |

| | | | | | | |
|---|---|---|---|---|---|---|
| Phytophthora Gene | Rps1c, Rps3a | | Stem Canker Tolerance | | | |
| Rust Gene | | | Chloride Sensitivity | CLMS | | |
| SCN Res Source | 88788 | | RootKnot Nematode | | Sting Nematode | |
| R1 R2 R3 R5 | R7 R9 R14 | Incognita | Arenaria | Javanica | Pratylenchus | |
| FI % FI % FI % FI % | FI % FI % FI % | MI_U | | | | |

SCN = Soybean Cyst Nematode, RKN = Root Knot Nematode

Rps gene indicates the specific gene for resistance but if none are indicated then none are known to be present.

% Protein and % Oil are given at 13% moisture (standard moisture).

DAS-44406-6 indicates this variety carries the glyphosate, glufosinate, and 2,4-D tolerance cassette derived from event DAS-44406-6.

Seed shape: 1 = spherical; 2 = spherical-flattened; 3 = elongate; 4 = elongate-flattened Seed coat luster: 1 = dull; 2 = shiny Plant Morphological traits are listed in the order of flower, pubescence, pod color, and hilum. For flower, P—purple, W = white, and S = segregating (mixture of colors). For pubescence, G = gray, T = tawny, Lt = LT = light tawny, LBr = LB = light brown, and S = segregating (mixture of colors). For pod color, T = tan, B = brown, LBr = light brown, and S = segregating (mixture of colors). For hilum, G = gray, BR = Br = brown, MBr = medium brown, BF = Bf = buff, BL = Bl = black, IB = Ib = imperfect black, Y = yellow, IY = Iy = imperfect yellow, S = segregating (mixture of colors).

Leaf Color: 1 = light green; 2 = medium green; 3 = dark green

Ratings are on a 1 to 9 scale with 1 being the best.

Sting Nematode is Pratylenchus.

Chloride sensitivity: CL = chloride, M = molecular marker results, X = segregating, S = susceptible marker allele present, R = resistant marker allele present.

CLMS = chloride sensitive and CLMR = chloride resistant

MI_S = susceptible, MI_R = resistant, MI_MR = mixed resistance. MI_U = unable to determine

TABLE 2

| Agronomic and Disease Traits | | | | | | | | | | |
|---|---|---|---|---|---|---|---|---|---|---|
| VHNO | Yield | Emerge | HrvstLod | GrnLod | MatDays | Height | Canopy | Branch | GrnStem | IDC |
| EC2020142 | 51.1 | 2.3 | 3.7 | 4.0 | 116.0 | 27.6 | 5.5 | 6.8 | 1.5 | 4.1 |
| NK14-C7XF | 50.1 | 3.4 | 4.8 | 4.2 | 119.2 | 34.3 | 4.6 | 6.0 | 2.5 | 4.4 |
| NK10-W8XF | 50.8 | 2.0 | 4.8 | 4.0 | 113.8 | 30.0 | 5.5 | 4.7 | 1.0 | 3.9 |
| AG14XF2 | 51.6 | 1.9 | 4.7 | 3.3 | 116.8 | 31.5 | 4.7 | 4.8 | 1.0 | 3.5 |
| NK13-Y4XF | 51.3 | 3.1 | 3.7 | 2.8 | 117.9 | 32.5 | 4.6 | 5.5 | 1.5 | 4.0 |
| PXF 121 | 50.9 | 3.2 | 3.8 | 2.5 | 118.4 | 30.1 | 5.1 | 5.6 | 1.5 | 4.3 |
| DKB11-84 | 49.9 | 2.1 | 4.0 | 3.3 | 114.6 | 31.3 | 4.6 | 5.2 | 1.0 | 4.1 |
| Environments | 31.0 | 8.0 | 3.0 | 2.0 | 10.0 | 3.0 | 5.0 | 6.0 | 1.0 | 7.0 |
| Grand Mean | 51.0 | 2.7 | 3.9 | 3.4 | 117.2 | 30.6 | 5.0 | 5.9 | 1.6 | 4.0 |
| Check Mean | 51.0 | 2.7 | 4.0 | 3.4 | 116.8 | 30.8 | 5.1 | 5.7 | 1.6 | 4.0 |
| LSD (0.05) | 1.8 | 0.6 | 1.4 | 2.0 | 1.6 | 3.1 | 0.7 | 0.7 | 1.4 | 0.0 |

TABLE 2-continued

| | | | | Agronomic and Disease Traits | | | | | | |
|---|---|---|---|---|---|---|---|---|---|---|
| VHNO | BSR_R | CR_R | FELS | PM_R | PRR | BP_R | RUSTR | SDS | SWM | TSP_R |
| EC2020142 | #N/A | #N/A | 6.0 | #N/A | 1.5 | #N/A | #N/A | 5.0 | 5.2 | #N/A |
| NK14-C7XF | #N/A | #N/A | 5.0 | #N/A | 2.0 | #N/A | #N/A | 4.5 | 5.2 | #N/A |
| NK10-W8XF | #N/A | #N/A | 2.0 | #N/A | 1.8 | #N/A | #N/A | 2.8 | 3.9 | #N/A |
| AG14XF2 | #N/A | #N/A | 4.5 | #N/A | 2.3 | #N/A | #N/A | 4.3 | 5.0 | #N/A |
| NK13-Y4XF | #N/A | #N/A | 5.0 | #N/A | 1.8 | #N/A | #N/A | 3.8 | 3.3 | #N/A |
| PXF 121 | #N/A | #N/A | 7.0 | #N/A | 3.0 | #N/A | #N/A | 2.3 | 5.6 | #N/A |
| DKB11-84 | #N/A | #N/A | 6.5 | #N/A | 2.3 | #N/A | #N/A | 2.8 | 4.1 | #N/A |
| Environments | #N/A | #N/A | 1.0 | #N/A | 2.0 | #N/A | #N/A | 2.0 | 5.0 | #N/A |
| Grand Mean | #N/A | #N/A | 5.1 | #N/A | 1.9 | #N/A | #N/A | 4.2 | 4.9 | #N/A |
| Check Mean | #N/A | #N/A | 5.3 | #N/A | 1.9 | #N/A | #N/A | 4.1 | 4.8 | #N/A |
| LSD (0.05) | #N/A | #N/A | 1.4 | #N/A | 0.0 | #N/A | #N/A | 1.6 | 1.2 | #N/A |

N/A = no data available

As the previous table indicates, each of these lines has their own positive traits. Each of these lines is different from EC2020142. EC2020142 was tested by Syngenta Seeds, Inc. in Advanced Yield Trials in 2022. Data were collected for yield (bushels per acre), maturity date (95% mature pod color), harvest lodging (1=plant is upright to 9=plant is prostrate), and plant height in inches. EC2020142 is not significantly different for yield compared to NK14-C7XF, NK10-W8XF, and NK13-Y4XF (LSD 0.05=1.8 bu/ac). EC2020142 is not significantly different for harvest lodging compared to NK14-C7XF, NK10-W8XF, and NK13-Y4XF (LSD 0.05=1.4). EC2020142 has a significantly different maturity compared to NK14-C7XF, NK10-W8XF, and NK13-Y4XF (LSD 0.05=1.6 days). EC2020142 is not significantly different for plant height compared to NK10-W8XF and NK13-Y4XF. EC2020142 is significantly shorter than NK14-C7XF (LSD 0.05=3.1 days). EC2020142 is most similar to NK14-C7XF, NK10-W8XF, and NK13-Y4XF but can be differentiated by pubescence color. EC2020142 has gray pubescence color and NK14-C7XF, NK10-W8XF, and NK13-Y4XF have light tawny pubescence color.

EC2020188 is employed in a number of plot repetitions to establish trait characteristics.

EC2020188 is a novel soybean cultivar designated EC2020188 with high yield potential and tolerance to glyphosate, glufosinate, and 2,4-D herbicides. The invention relates to seeds of the cultivars EC2020188, plants of the cultivars EC2020188 and to methods for producing a soybean plant produced by crossing the soybean EC2020188 by itself or another soybean genotype.

EC2020188 is a Group 1 soybean cultivar. This variety has an RM of 1.600. To be sold commercially in the United States and Canada where Maturity Group 1 soybeans are grown. Specific areas where best adaption occurs includes Ontario, Iowa, Minnesota, and South Dakota. The target for this variety is geographic regions that grow Group 1 maturity glyphosate, glufosinate, and 2,4-D tolerant varieties. EC2020188 is an elite soybean line originating from a cross between NE1406086 (not commercially available) and 14531823-09 E3 (not commercially available) via backcross breeding.

The characteristics and traits EC2020188 are listed below.

TABLE 3

| | | CHARACTERISTICS AND TRAITS | | | |
|---|---|---|---|---|---|
| Herbicide Transgene | | DAS-44406-6 | | | |
| Insect Transgene | | | | | |
| Other Transgene | | | | Relative Maturity | 1.600 |
| Sulfonylurea Tolerance | N | Seed Shape | | Hypocotyl Color | |
| Metribuzin Tolerance | MET_R | Seed Coat Luster | | Plant Morphological | PGTIb |
| Aphid Gene | Rag1_S | Peroxidase | | Leaf Color | |
| % Protein @ 13% mst | | Seed Size g/100 seeds | | Leaf Shape | |
| % Oil @13% mst | | Growth Habit | INDET | Calculated Leaf Shape | |

TABLE 3-continued

CHARACTERISTICS AND TRAITS

Plant Health

| Phytophthora Gene | | | | | Rps1c, Rps3a | | Stem Canker Tolerance | | | |
|---|---|---|---|---|---|---|---|---|---|---|
| Rust Gene | | | | | | | Chloride Sensitivity | CLMS | | |
| SCN Res Source | | | | | PEK | | RootKnot Nematode | | | Sting Nematode |
| R1 FI% | R2 FI% | R3 F1% | R5 F1% | R7 F1% | R9 F1% | R14 FI% | Incognita ML_U | Arenaria | Javanica | Pratylenchus |

SCN = Soybean Cyst Nematode, RKN = Root Knot Nematode

Rps gene indicates the specific gene for resistance but if none are indicated then none are known to be present.

% Protein and % Oil are given at 13% moisture (standard moisture).

DAS-44406-6 indicates this variety carries the glyphosate, glufosinate, and 2,4-D tolerance cassette derived from event DAS-44406-6.

Seed shape: 1 = spherical; 2 = spherical-flattened; 3 = elongate; 4 = elongate-flattened Seed coat luster: 1 = dull; 2 = shiny Plant Morphological traits are listed in the order of flower, pubescence, pod color, and hilum. For flower, P–purple, W = white, and S = segregating (mixture of colors). For pubescence, G = gray, T = tawny, Lt = LT = light tawny, LBr = LB = light brown, and S = segregating (mixture of colors). For pod color, T = tan, B = brown, LBr = light brown, and S = segregating (mixture of colors). For hilum, G = gray, BR = Br = brown, MBr = medium brown, BF = Bf = buff, BL = Bl = black, IB = Ib = imperfect black, Y = yellow, IY = Iy = imperfect yellow, S = segregating (mixture of colors).

Leaf Color: 1 = light green; 2 = medium green; 3 = dark green

Ratings are on a 1 to 9 scale with 1 being the best.

Sting Nematode is Pratylenchus.

Chloride sensitivity: CL = chloride, M = molecular marker results, X = segregating, S = susceptible marker allele present, R = resistant marker allele present.

CLMS = chloride sensitive and CLMR = chloride resistant

ML_S = susceptible, ML_R = resistant, ML_MR = mixed resistance. ML_U = unable to determine

TABLE 4

Agronomic and Disease Traits

| VHNO | Yield | Emerge | HrvstLod | GrnLod | MatDays | Height | Canopy | Branch | GrnStem | IDC |
|---|---|---|---|---|---|---|---|---|---|---|
| NK20-B6E3S | 59.2 | 2.8 | 2.8 | 1.3 | 117.6 | 31.0 | 6.4 | 6.5 | 2.0 | 4.0 |
| PE 1501 | 59.8 | 3.1 | 3.0 | 2.5 | 114.4 | 31.7 | 5.8 | 6.1 | 1.3 | 4.1 |
| NK18-J7E3 | 59.3 | 3.0 | 3.8 | 3.4 | 117.1 | 34.9 | 5.9 | 5.9 | 2.0 | 3.5 |
| PXF 152 | 57.2 | 2.9 | 2.8 | 2.6 | 113.2 | 32.6 | 5.1 | 5.6 | 1.0 | 3.6 |
| DKB14-65 | 54.8 | 2.4 | 3.9 | 3.9 | 113.7 | 34.1 | 5.3 | 4.2 | 1.6 | 4.9 |
| P18A33X | 59.5 | 2.0 | 3.0 | 2.8 | 117.3 | 33.4 | 5.7 | 4.9 | 1.3 | 4.0 |
| EC2020188 | 58.9 | 1.5 | 3.1 | 2.3 | 113.1 | 31.2 | 5.9 | 6.4 | 1.3 | 3.5 |
| Environments | 42.0 | 9.0 | 6.0 | 6.0 | 9.0 | 5.0 | 9.0 | 7.0 | 3.0 | 6.0 |
| Grand Mean | 58.5 | 2.7 | 3.0 | 2.5 | 115.1 | 33.1 | 5.5 | 5.9 | 1.9 | 4.0 |
| Check Mean | 58.4 | 2.6 | 3.1 | 2.7 | 115.0 | 33.4 | 5.5 | 5.6 | 1.9 | 3.9 |
| LSD (0.05) | 1.6 | 0.5 | 0.7 | 0.8 | 1.5 | 2.1 | 0.6 | 0.7 | 0.9 | 1.5 |

| VHNO | BSR_R | CR_R | FELS | PM_R | PRR | BP_R | RUSTR | SDS | SWM | TSP_R |
|---|---|---|---|---|---|---|---|---|---|---|
| NK20-B6E3S | #N/A | #N/A | 3.5 | #N/A | 2.7 | #N/A | #N/A | 2.4 | 6.2 | #N/A |
| PE 1501 | #N/A | #N/A | 4.5 | #N/A | 2.0 | #N/A | #N/A | 2.3 | 4.5 | #N/A |
| NK18-J7E3 | #N/A | #N/A | 4.0 | #N/A | 1.7 | #N/A | #N/A | 2.5 | 3.9 | #N/A |
| PXF 152 | #N/A | #N/A | 3.5 | #N/A | 1.3 | #N/A | #N/A | 2.8 | 3.2 | #N/A |
| DKB14-65 | #N/A | #N/A | 4.5 | #N/A | 1.0 | #N/A | #N/A | 2.9 | 3.4 | #N/A |
| P18A33X | #N/A | #N/A | 3.0 | #N/A | 1.7 | #N/A | #N/A | 1.3 | 3.3 | #N/A |
| EC2020188 | #N/A | #N/A | 3.5 | #N/A | 1.7 | #N/A | #N/A | 2.4 | 4.3 | #N/A |
| Environments | #N/A | #N/A | 1.0 | #N/A | 1.0 | #N/A | #N/A | 7.0 | 5.0 | #N/A |
| Grand Mean | #N/A | #N/A | 4.1 | #N/A | 2.3 | #N/A | #N/A | 2.5 | 4.6 | #N/A |
| Check Mean | #N/A | #N/A | 4.1 | #N/A | 2.1 | #N/A | #N/A | 2.5 | 4.6 | #N/A |
| LSD (0.05) | #N/A | #N/A | 0.0 | #N/A | 0.0 | #N/A | #N/A | 0.9 | 1.3 | #N/A |

N/A = no data available

As the previous table indicates each of these lines has their own positive traits. Each of these lines is different from EC2020188. EC2020188 was tested by Syngenta Seeds, Inc. in Advanced Yield Trials in 2022. Data were collected for yield (bushels per acre), maturity date (95% mature pod color), harvest lodging (1=plant is upright to 9=plant is prostrate), and plant height in inches. EC2020188 is not significantly different for yield compared to NK20-B6E3S and NK18-J7E3 (LSD 0.05=1.6 bu/ac). EC2020188 is not significantly different for harvest lodging compared to NK20-B6E3S and NK18-J7E3 (LSD 0.05=0.7). EC2020188 is significantly earlier for maturity compared to NK20-B6E3S and NK18-J7E3 (LSD 0.05=1.5 days). EC2020188 is not significantly different for plant height compared to NK20-B6E3S and NK18-J7E3 (LSD 0.05=2.1 inches). EC2020188 is most similar to NK18-J7E3 but can be differentiated by pod color. EC2020188 has tan pod color and NK18-J7E3 has brown pod color. EC2020188 is most similar to NK20-B6E3S but can be differentiated by resistance to *Phytophthora sojae*. EC2020188 has Rps 1c and Rps 3a resistance alleles and NK20-B6E3S only has the Rps 1c resistance allele.

EC2020491 is employed in a number of plot repetitions to establish trait characteristics.

EC2020491 is a novel soybean cultivar designated with high yield potential and tolerance to sulfonylurea, glyphosate, 2,4-D, and glufosinate herbicides. The invention relates to seeds of the cultivars EC2020491, plants of the cultivars EC2020491 and to methods for producing a soybean plant produced by crossing the soybean EC2020491 by itself or another soybean genotype.

EC2020491 is a Group 1 soybean cultivar. This variety has an RM of 1.900. To be sold commercially in the United States and Canada where Maturity Group 1 soybeans are grown. Specific areas where best adaption occurs includes Ontario, Iowa, Minnesota, South Dakota. The target for this variety is geographic regions that grow Group 1 maturity sulfonylurea, glyphosate, 2,4-D, and The characteristics and traits of EC2020491 are listed below.

TABLE 5

CHARACTERISTICS AND TRAITS

| Herbicide Transgene | | | DAS-44406-6 | | | |
|---|---|---|---|---|---|---|
| Insect Transgene | | | | | | |
| Other Transgene | | | | | Relative Maturity | 1.900 |
| Sulfonylurea Tolerance | Y | | Seed Shape | | Hypocotyl Color | |
| Metribuzin Tolerance | MET_R | | Seed Coat Luster | | Plant Morphological | PGBIb |
| Aphid Gene | Rag1_S | | Peroxidase | | Leaf Color | |
| % Protein @ 13% mst | | | Seed Size g/100 seeds | | Leaf Shape Calculated | |
| % Oil @13% mst | | | Growth Habit | INDET | Leaf Shape | |
| | | Plant Health | | | | |

| | | | | | | | | | | |
|---|---|---|---|---|---|---|---|---|---|---|
| | Phytophthora Gene | | Rps1k | | Stem Canker Tolerance | | | | | |
| | Rust Gene | | | | Chloride Sensitivity | CLMS | | | | |
| | SCN Res Source | | 88788 | | RootKnot Nematode | | | Sting Nematode | | |
| R1 FI% | R2 F1% | R3 FI% | R5 FI% | R7 F1% | R9 F1% | R14 FI% | Incognita | Arenaria | Javanica | Pratylenchus |
| | | | | | | | MI_U | | | |

SCN = Soybean Cyst Nematode, RKN = Root Knot Nematode
Rps gene indicates the specific gene for resistance but if none are indicated then none are known to be present.
% Protein and % Oil are given at 13% moisture (standard moisture).
DAS-44406-6 indicates this variety carries the glyphosate, glufosinate, and 2,4-D tolerance cassette derived from event DAS-44406-6.
Seed shape: 1 = spherical; 2 = spherical-flattened; 3 = elongate; 4 = elongate-flattened
Seed coat luster: 1 = dull; 2 = shiny
Plant Morphological traits are listed in the order of flower, pubescence, pod color, and hilum. For flower, P—purple, W = white, and S = segregating (mixture of colors). For pubescence, G = gray, T = tawny, Lt = LT = light tawny, LBr = LB = light brown, and S = segregating (mixture of colors). For pod color, T = tan, B = brown, LBr = light brown, and S = segregating (mixture of colors). For hilum, G = gray, BR = Br = brown, MBr = medium brown, BF = Bf = buff, BL = Bl = black, IB = Ib= imperfect black, Y = yellow, IY = Iy = imperfect yellow, S = segregating (mixture of colors).
Leaf Color: 1 = light green; 2 = medium green; 3 = dark green
Ratings are on a 1 to 9 scale with 1 being the best.
Sting Nematode is Pratylenchus.
Chloride sensitivity: CL = chloride, M = molecular marker results, X = segregating, S = susceptible marker allele present, R = resistant marker allele present.
CLMS = chloride sensitive and CLMR = chloride resistant
MI_S = susceptible, MI_R = resistant, MI_MR = mixed resistance. MI_U = unable to determine

TABLE 6

Agronomic and Disease Traits

| VHNO | Yield | Emerge | HrvstLod | GrnLod | MatDays | Height | Canopy | Branch | GrnStem | IDC |
|---|---|---|---|---|---|---|---|---|---|---|
| NK20-B6E3S | 59.2 | 2.8 | 2.8 | 1.3 | 117.6 | 31.0 | 6.4 | 6.5 | 2.0 | 4.0 |
| PE 1501 | 59.8 | 3.1 | 3.0 | 2.5 | 114.4 | 31.7 | 5.8 | 6.1 | 1.3 | 4.1 |
| NK18-J7E3 | 59.3 | 3.0 | 3.8 | 3.4 | 117.1 | 34.9 | 5.9 | 5.9 | 2.0 | 3.5 |
| PXF 152 | 57.2 | 2.9 | 2.8 | 2.6 | 113.2 | 32.6 | 5.1 | 5.6 | 1.0 | 3.6 |
| DKB14-65 | 54.8 | 2.4 | 3.9 | 3.9 | 113.7 | 34.1 | 5.3 | 4.2 | 1.6 | 4.9 |
| P18A33X | 59.5 | 2.0 | 3.0 | 2.8 | 117.3 | 33.4 | 5.7 | 4.9 | 1.3 | 4.0 |
| EC2020491 | 59.8 | 3.3 | 2.8 | 2.0 | 117.1 | 32.1 | 5.8 | 6.9 | 2.2 | 4.3 |
| Environments | 42.0 | 9.0 | 6.0 | 6.0 | 9.0 | 5.0 | 9.0 | 7.0 | 3.0 | 6.0 |
| Grand Mean | 58.5 | 2.7 | 3.0 | 2.5 | 115.1 | 33.1 | 5.5 | 5.9 | 1.9 | 4.0 |
| Check Mean | 58.4 | 2.6 | 3.1 | 2.7 | 115.0 | 33.4 | 5.5 | 5.6 | 1.9 | 3.9 |
| LSD (0.05) | 1.6 | 0.5 | 0.7 | 0.8 | 1.5 | 2.1 | 0.6 | 0.7 | 0.9 | 1.5 |

| VHNO | BSR_R | CR_R | FELS | PM_R | PRR | BP_R | RUSTR | SDS | SWM | TSP_R |
|---|---|---|---|---|---|---|---|---|---|---|
| NK20-B6E3S | #N/A | #N/A | 3.5 | #N/A | 2.7 | #N/A | #N/A | 2.4 | 6.2 | #N/A |
| PE 1501 | #N/A | #N/A | 4.5 | #N/A | 2.0 | #N/A | #N/A | 2.3 | 4.5 | #N/A |
| NK18-J7E3 | #N/A | #N/A | 4.0 | #N/A | 1.7 | #N/A | #N/A | 2.5 | 3.9 | #N/A |
| PXF 152 | #N/A | #N/A | 3.5 | #N/A | 1.3 | #N/A | #N/A | 2.8 | 3.2 | #N/A |
| DKB14-65 | #N/A | #N/A | 4.5 | #N/A | 1.0 | #N/A | #N/A | 2.9 | 3.4 | #N/A |
| P18A33X | #N/A | #N/A | 3.0 | #N/A | 1.7 | #N/A | #N/A | 1.3 | 3.3 | #N/A |
| EC2020491 | #N/A | #N/A | 4.5 | #N/A | 2.6 | #N/A | #N/A | 2.6 | 5.2 | #N/A |
| Environments | #N/A | #N/A | 1.0 | #N/A | 1.0 | #N/A | #N/A | 7.0 | 5.0 | #N/A |
| Grand Mean | #N/A | #N/A | 4.1 | #N/A | 2.3 | #N/A | #N/A | 2.5 | 4.6 | #N/A |
| Check Mean | #N/A | #N/A | 4.1 | #N/A | 2.1 | #N/A | #N/A | 2.5 | 4.6 | #N/A |
| LSD (0.05) | #N/A | #N/A | 0.0 | #N/A | 0.0 | #N/A | #N/A | 0.9 | 1.3 | #N/A |

N/A = no data available

As the previous table indicates each of these lines has their own positive traits. Each of these lines is different from EC2020491. EC2020491 was tested by Syngenta Seeds, Inc. in Advanced Yield Trials in 2021 and 2022. Data were collected for yield (bushels per acre), maturity date (95% mature pod color), harvest lodging (1=plant is upright to 9=plant is prostrate), and plant height in inches. EC2020491 is not significantly different for yield compared to NK20-B6E3S and NK18-J7E3 (LSD 0.05=1.6 bu/ac). EC2020491 is not significantly different for harvest lodging compared to NK20-B6E3S. EC2020491 is significantly better for harvest lodging than NK18-J7E3 (LSD 0.05=0.7). EC2020491 is not significantly different for maturity compared to NK20-B6E3S and NK18-J7E3 (LSD 0.05=1.5 days). EC2020491 is not significantly different for plant height compared to NK20-B6E3S. EC2020491 is significantly shorter than NK18-J7E3 (LSD 0.05=2.1 inches). EC2020491 is most similar to NK20-B6E3S but can be differentiated by pod color. EC2020491 has brown pod color and NK20-B6E3S has tan pod color. EC2020491 is most similar to NK18-J7E3 but can be differentiated by resistance to *Phytophthora sojae*. EC2020491 has the Rps 1k allele and NK18-J7E3 has the Rps 1c allele.

EC2140213 is employed in a number of plot repetitions to establish trait characteristics.

EC2140213 is a novel soybean cultivar designated EC2140213 with high yield potential and tolerance to glyphosate, glufosinate, and dicamba herbicides. The invention relates to seeds of the cultivars EC2140213, plants of the cultivars EC2140213 and to methods for producing a soybean plant produced by crossing the soybean EC2140213 by itself or another soybean genotype.

EC2140213 is a Group 2 soybean cultivar. This variety has an RM of 2.200. To be sold commercially in the United States where Maturity Group 2 soybeans are grown. Specific areas where best adaption occurs includes Illinois, Iowa, and Nebraska. The target for this variety is geographic regions that grow Group 2 maturity glyphosate, glufosinate, and dicamba tolerant soybeans.

The characteristics and traits of EC2140213 are listed below.

TABLE 7

| CHARACTERISTICS AND TRAITS | | | | | |
|---|---|---|---|---|---|
| Herbicide Transgene | | A5547-127; MON 87708; MON 89788 | | | |
| Insect Transgene | | | | | |
| Other Transgene | | | | Relative Maturity | 2.200 |
| Sulfonylurea Tolerance | N | | Seed Shape | Hypocotyl Color | |
| Metribuzin Tolerance | MET_R | | Seed Coat Luster | Plant Morphological | WLBBl |
| Aphid Gene | | | Peroxidase | Leaf Color | |
| % Protein @ 13% mst | | | Seed Size g/100 seeds | Leaf Shape Calculated | |
| % Oil @13% mst | | | Growth Habit | INDET | Leaf Shape |
| | | Plant Health | | | |
| Phytophthora Gene | | Rps1c | | Stem Canker Tolerance | |
| Rust Gene | | | | Chloride Sensitivity | CLMS |
| SCN Res Source | | 88788 | | RootKnot Nematode | Sting Nematode |
| R1 FI% R2 FI% R3 FI% R5 FI% R7 FI% | R9 FI% | R14 FI% | Incognita Arenaria Javanica | Pratylenchus | |

SCN = Soybean Cyst Nematode, RKN = Root Knot Nematode
Rps gene indicates the specific gene for resistance but if none are indicated then none are known to be present.
% Protein and % Oil are given at 13% moisture (standard moisture).
A5547-127 indicates this variety carries the glufosinate tolerance transgene derived from event A5547-127.
MON89788 indicates this variety carries the glyphosate tolerance transgene derived from event MON 89788.
MON87708 indicates this variety carries the dicamba tolerance transgene derived from event MON 87708.
Seed shape: 1 = spherical; 2 = spherical-flattened; 3 = elongate; 4 = elongate-flattened
Seed coat luster: 1 = dull; 2 = shiny
Plant Morphological traits are listed in the order of flower, pubescence, pod color, and hilum. For flower, P—purple, W = white, and S = segregating (mixture of colors). For pubescence, G = gray, T = tawny, Lt = LT = light tawny, LBr = LB = light brown, and S = segregating (mixture of colors). For pod color, T = tan, B = brown, LBr = light brown, and S = segregating (mixture of colors). For hilum, G = gray, BR = Br = brown, MBr = medium brown, BF = Bf = buff, BL = Bl = black, IB = Ib = imperfect black, Y = yellow, IY = Iy = imperfect yellow, S = segregating (mixture of colors).
Leaf Color: 1 = light green; 2 = medium green; 3 = dark green
Ratings are on a 1 to 9 scale with 1 being the best.
Sting Nematode is Pratylenchus.
Chloride sensitivity: CL = chloride, M = molecular marker results, X = segregating, S = susceptible marker allele present, R = resistant marker allele present.
CLMS = chloride sensitive and CLMR = chloride resistant
ML_S = susceptible, ML_R = resistant, ML_MR = mixed resistance. ML_U = unable to determine

TABLE 8

| Agronomic and Disease Traits | | | | | | | | | | |
|---|---|---|---|---|---|---|---|---|---|---|
| VHNO | Yield | Emerge | HrvstLod | GrnLod | MatDays | Height | Canopy | Branch | GrnStem | IDC |
| NK22-R2E3S | 61.2 | 2.5 | 2.0 | 1.4 | 118.4 | 35.0 | 5.9 | 6.5 | 1.0 | 3.5 |
| NK19-Y5E3 | 62.2 | 2.5 | 3.2 | 2.0 | 119.1 | 35.4 | 4.6 | 6.0 | 1.0 | 3.9 |
| NK20-B6E3S | 63.9 | 2.9 | 2.2 | 1.3 | 117.7 | 30.5 | 6.4 | 6.3 | 1.0 | 3.1 |
| EC2140213 | 64.5 | 2.9 | 2.7 | 2.7 | 120.3 | 35.5 | 6.8 | 5.0 | 2.0 | 3.3 |
| NK19-T8E3S | 61.6 | 3.0 | 2.8 | 1.4 | 116.5 | 31.1 | 5.4 | 7.0 | 1.0 | 4.1 |
| GS2243E3S | 63.7 | 2.8 | 2.2 | 1.5 | 117.8 | 34.1 | 6.4 | 5.8 | 1.0 | 4.8 |
| GH2292E3 | 63.5 | 2.8 | 2.8 | 1.8 | 118.7 | 32.6 | 5.8 | 6.8 | 1.0 | 3.1 |
| Environments | 28.0 | 5.0 | 3.0 | 5.0 | 9.0 | 3.0 | 7.0 | 3.0 | 1.0 | 4.0 |
| Grand Mean | 62.5 | 2.8 | 2.8 | 2.0 | 118.7 | 33.4 | 5.7 | 5.7 | 1.3 | 3.7 |

TABLE 8-continued

| Agronomic and Disease Traits | | | | | | | | | |
|---|---|---|---|---|---|---|---|---|---|
| Check Mean | 63.3 | 2.9 | 2.7 | 1.9 | 118.6 | 33.6 | 5.9 | 6.1 | 1.0 | 3.8 |
| LSD (0.05) | 2.6 | 0.5 | 1.3 | 0.8 | 1.7 | 2.7 | 0.7 | 1.5 | 0.0 | 0.9 |

| VHNO | BSR_R | CR_R | FELS | PM_R | PRR | BP_R | RUSTR | SDS | SWM | TSP_R |
|---|---|---|---|---|---|---|---|---|---|---|
| NK22-R2E3S | #N/A | #N/A | 5.0 | #N/A | 2.0 | #N/A | #N/A | 3.0 | 5.6 | #N/A |
| NK19-Y5E3 | #N/A | #N/A | 4.3 | #N/A | 2.5 | #N/A | #N/A | 3.5 | 4.5 | #N/A |
| NK20-B6E3S | #N/A | #N/A | 4.0 | #N/A | 3.5 | #N/A | #N/A | 2.3 | 5.7 | #N/A |
| EC2140213 | #N/A | #N/A | 4.8 | #N/A | 2.5 | #N/A | #N/A | 2.0 | 4.4 | #N/A |
| NK19-T8E3S | #N/A | #N/A | 4.8 | #N/A | 3.5 | #N/A | #N/A | 4.3 | 4.4 | #N/A |
| GS2243E3S | #N/A | #N/A | 5.0 | #N/A | 3.5 | #N/A | #N/A | 3.0 | 5.3 | #N/A |
| GH2292E3 | #N/A | #N/A | 3.3 | #N/A | 1.5 | #N/A | #N/A | 1.7 | 4.2 | #N/A |
| Environments | #N/A | #N/A | 2.0 | #N/A | 1.0 | #N/A | #N/A | 4.0 | 4.0 | #N/A |
| Grand Mean | #N/A | #N/A | 4.4 | #N/A | 2.5 | #N/A | #N/A | 2.9 | 4.8 | #N/A |
| Check Mean | #N/A | #N/A | 4.2 | #N/A | 2.5 | #N/A | #N/A | 2.5 | 4.7 | #N/A |
| LSD (0.05) | #N/A | #N/A | 1.4 | #N/A | 0.0 | #N/A | #N/A | 1.5 | 1.4 | #N/A |

N/A = no data available

As the previous table indicates each of these lines has their own positive traits. Each of these lines is different from EC2140213. EC2140213 was tested by Syngenta Seeds, Inc. in Advanced Yield Trials in 2022. Data were collected for yield (bushels per acre), maturity date (95% mature pod color), harvest lodging (1=plant is upright to 9=plant is prostrate), and plant height in inches. EC2140213 is not significantly different for yield compared to NK19-Y5E3, NK20-B6E3S, GS2243E3, and GH2292E3. EC2140213 has significantly higher yield than NK22-R2E3 and NK19-T8E3S (LSD 0.05=2.6 bu/ac). EC2140213 is not significantly different for harvest lodging compared to NK22-R2E3S, NK19-Y5E3, NK20-B6E3S, NK19-T8E3S, GS2243E3S, and GH2292E3 (LSD 0.05=1.3). EC2140213 is not significantly different for maturity compared to NK19-Y5E3, NK20-B6E3S, and GH2292E3. EC2140213 is significantly later than NK22-R2E3S, NK19-T8E3S, and GS2243E3S (LSD 0.05=1.7 days). EC2140213 is not significantly different for plant height compared to NK22-R2E3, NK19-Y5E3, and GS2243E3S. EC2140213 is significantly taller than NK20-B6E3S, NK19-T8E3S, and GH2292E3 (LSD 0.05=2.7 inches). EC2140213 is most similar to NK22-R2E3S, NK20-B6E3S, NK19-T8E3S, GS2243E3S, and GH2292E3 but can be differentiated by pubescence color. EC2140213 has light tawny pubescence color and NK22-R2E3S, NK20-B6E3S, NK19-T8E3S, GS2243E3S, and GH2292E3 have gray pubescence color. EC2140213 is most similar to NK19-Y5E3 but can be differentiated by resistance to *Phytophthora sojae*. EC2140213 has the Rps1c allele and NK19-Y5E3 has the Rps1k allele.

EC2021110 is employed in a number of plot repetitions to establish trait characteristics.

EC2021110 is a novel soybean cultivar designated EC2021110 with high yield potential and tolerance to glyphosate, glufosinate, and 2,4-D herbicides. The invention relates to seeds of the cultivars EC2021110, plants of the cultivars EC2021110 and to methods for producing a soybean plant produced by crossing the soybean EC2021110 by itself or another soybean genotype.

EC2021110 is a Group 2 soybean cultivar. This variety has an RM of 2.400. To be sold commercially in the United States where Maturity Group II soybeans are grown. Specific areas where best adaption occurs includes Illinois, Iowa, and Nebraska. The target for this variety is geographic regions that grow Group II maturity glyphosate, 2,4-D, and glufosinate tolerant soybeans.

The characteristics and traits of EC2021110 are listed below.

TABLE 9

| CHARACTERISTICS AND TRAITS | | | | |
|---|---|---|---|---|
| Herbicide Transgene | | DAS-44406-6 | | |
| Insect Transgene | | | | |
| Other Transgene | | | Relative Maturity | 2.400 |
| Sulfonylurea Tolerance | N | Seed Shape | Hypocotyl Color | |
| Metribuzin Tolerance | MET_R | Seed Coat Luster | Plant Morphological | PGTIb |
| Aphid Gene | Rag1_S | Peroxidase | Leaf Color | |
| % Protein @ 13% mst | | Seed Size g/100 seeds | Leaf Shape Calculated | |
| % Oil @13% mst | | Growth Habit | INDET | Leaf shape |

TABLE 9-continued

CHARACTERISTICS AND TRAITS

Plant Health

| R1 FI% | Phytophthora Gene Rust Gene SCN Res Source R2 FI% R3 FI% | R5 F1% R7 F1% | Rps1k 88788 R9 FI% R14 FI% | Stem Canker Tolerance Chloride Sensitivity CLMS RootKnot Nematode Incognita Arenaria Javanica MI_U | Sting Nematode Pratylenchus |
|---|---|---|---|---|---|

SCN = Soybean Cyst Nematode, RKN = Root Knot Nematode

Rps gene indicates the specific gene for resistance but if none are indicated then none are known to be present.

% Protein and % Oil are given at 13% moisture (standard moisture).

DAS-44406-6 indicates this variety carries the glyphosate, glufosinate, and 2,4-D tolerance cassette derived from event DAS-44406-6.

Seed shape: 1 = spherical; 2 = spherical-flattened; 3 = elongate; 4 = elongate-flattened Seed coat luster: 1 = dull; 2 = shiny Plant Morphological traits are listed in the order of flower, pubescence, pod color, and hilum. For flower, P—purple, W = white, and S = segregating (mixture of colors). For pubescence, G = gray, T = tawny, Lt = LT = light tawny, LBr = LB = light brown, and S = segregating (mixture of colors). For pod color, T = tan, B = brown, LBr = light brown, and S = segregating (mixture of colors). For hilum, G = gray, BR = Br = brown, MBr = medium brown, BF = Bf = buff, BL = Bl = black, IB = Ib = imperfect black, Y = yellow, IY = Iy = imperfect yellow, S = segregating (mixture of colors).

Leaf Color: 1 = light green; 2 = medium green; 3 = dark green

Ratings are on a 1 to 9 scale with 1 being the best.

Sting Nematode is Pratylenchus.

Chloride sensitivity: CL = chloride, M = molecular marker results, X = segregating, S = susceptible marker allele present, R = resistant marker allele present.

CLMS = chloride sensitive and CLMR = chloride resistant

MI_S = susceptible, MI_R = resistant, MI_MR = mixed resistance. MI_U = unable to determine

TABLE 10

Agronomic and Disease Traits

| VHNO | Yield | Emerge | HrvstLod | GrnLod | MatDays | Height | Canopy | Branch | GrnStem | IDC |
|---|---|---|---|---|---|---|---|---|---|---|
| GS2243E3S | 61.7 | 2.0 | 2.1 | 1.9 | 118.1 | 33.9 | 5.9 | 5.7 | 1.8 | 3.8 |
| PE 2100 | 62.0 | 2.1 | 3.4 | 2.9 | 118.6 | 33.5 | 5.2 | 5.7 | 1.8 | 3.7 |
| AG23XF2 | 60.3 | 2.4 | 2.2 | 3.1 | 118.3 | 35.8 | 5.1 | 4.3 | 1.7 | 2.7 |
| NK23-T9XF | 63.2 | 3.4 | 3.1 | 2.9 | 122.1 | 33.8 | 6.4 | 5.8 | 2.5 | 3.5 |
| NK22-C4E3 | 59.6 | 3.3 | 3.1 | 2.6 | 119.5 | 34.1 | 5.7 | 6.7 | 1.7 | 2.8 |
| NK20-B6E3S | 61.7 | 2.0 | 1.8 | 1.8 | 118.1 | 28.8 | 5.8 | 6.3 | 1.7 | 3.3 |
| EC2021110 | #N/A | #N/A | #N/A | #N/A | #N/A | #N/A | #N/A | #N/A | #N/A | #N/A |
| Environments | 42.0 | 8.0 | 7.0 | 9.0 | 10.0 | 6.0 | 10.0 | 6.0 | 3.0 | 4.0 |
| Grand Mean | 61.6 | 2.6 | 2.9 | 2.4 | 119.4 | 33.8 | 5.6 | 5.6 | 2.1 | 3.3 |
| Check Mean | 61.5 | 2.5 | 3.0 | 2.6 | 119.4 | 34.0 | 5.7 | 5.7 | 2.1 | 3.2 |
| LSD (0.05) | 1.8 | 0.4 | 0.8 | 0.6 | 1.3 | 1.8 | 0.7 | 1.0 | 0.0 | 0.7 |

| VHNO | BSR_R | CR_R | FELS | PM_R | PRR | BP_R | RUSTR | SDS | SWM | TSP_R |
|---|---|---|---|---|---|---|---|---|---|---|
| GS2243E3S | #N/A | #N/A | 5.0 | #N/A | 2.7 | #N/A | #N/A | 3.0 | 6.0 | #N/A |
| PE 2100 | #N/A | #N/A | 3.5 | #N/A | 2.0 | #N/A | #N/A | 2.3 | 4.8 | #N/A |
| AG23XF2 | #N/A | #N/A | 3.0 | #N/A | 1.0 | #N/A | #N/A | 3.0 | 4.1 | #N/A |
| NK23-T9XF | #N/A | #N/A | 4.3 | #N/A | 2.7 | #N/A | #N/A | 2.4 | 5.4 | #N/A |
| NK22-C4E3 | #N/A | #N/A | 3.0 | #N/A | 2.0 | #N/A | #N/A | 2.7 | 4.2 | #N/A |
| NK20-B6E3S | #N/A | #N/A | 3.8 | #N/A | 4.0 | #N/A | #N/A | 1.9 | 6.3 | #N/A |
| EC2021110 | #N/A | #N/A | N/A | #N/A | #N/A | #N/A | #N/A | #N/A | #N/A | #N/A |
| Environments | #N/A | #N/A | 2.0 | #N/A | 1.0 | #N/A | #N/A | 5.0 | 4.0 | #N/A |
| Grand Mean | #N/A | #N/A | 4.0 | #N/A | 2.3 | #N/A | #N/A | 2.3 | 5.0 | #N/A |
| Check Mean | #N/A | #N/A | 4.0 | #N/A | 2.3 | #N/A | #N/A | 2.2 | 4.9 | #N/A |
| LSD (0.05) | #N/A | #N/A | 0.0 | #N/A | 1.7 | #N/A | #N/A | 0.8 | 1.4 | #N/A |

N/A = no data available

As the previous table indicates each of these lines has their own positive traits. Each of these lines is different from EC2021110. EC2021110 was tested by Syngenta Seeds, Inc. in Advanced Yield Trials in 2022. Data were collected for yield (bushels per acre), maturity date (95% mature pod color), harvest lodging (1=plant is upright to 9=plant is prostrate), and plant height in inches. EC2021110 is not significantly different for yield compared to GS2243E3S, NK23-T9XF, NK22-C4E3, and NK20-B6E3S (LSD 0.05=1.8 bu/ac). EC2021110 is not significantly different for harvest lodging compared to GS2243E3S, NK23-T9XF, and NK22-C4E3. EC2021110 is significantly different for harvest lodging than NK20-B6E3S (LSD 0.05=0.8).

EC2021110 is not significantly different for maturity than NK23-T9XF. EC2021110 is significantly later for maturity than GS2243E3S, NK22-C4E3, and NK20-B6E3S (LSD 0.05=1.3 days). EC2021110 is significantly taller than GS2243E3S, NK23-T9XF, NK22-C4E3, and NK20-B6E3S (LSD 0.05=1.8 inches). EC2021110 is most similar to NK23-T9XF but can be differentiated by pubescence color. EC2021110 has gray pubescence color and NK23-T9XF has light tawny pubescence color. EC2021110 is most similar to NK22-C4E3 but can be differentiated by pod color. EC2021110 has tan pod color and NK22-C4E3 has brown pod color. EC2021110 is most similar to GS2243E3S and NK20-B6E3S but can be differentiated by resistance to

*Phytophthora sojae*. EC2021110 has the Rps 1k resistance allele and GS2243E3S and NK20-B6E3S have the Rps 1c resistance allele.

EC2121951 is employed in a number of plot repetitions to establish trait characteristics.

EC2121951 is a novel soybean cultivar designated EC2121951 with high yield potential and tolerance to sulfonylurea, glyphosate, 2,4-D, and glufosinate herbicides. The invention relates to seeds of the cultivars EC2121951, plants of the cultivars EC2121951 and to methods for producing a soybean plant produced by crossing the soybean EC2121951 by itself or another soybean genotype.

EC2121951 is a Group 2 soybean cultivar. This variety has an RM of 2.800. To be sold commercially in the United States and Canada where Maturity Group 2 soybeans are grown. Specific areas where best adaption occurs includes Ontario, Illinois, Iowa, and Nebraska. The target for this variety is geographic regions that grow Group 2 maturity glyphosate, 2,4-D, and glufosinate tolerant soybeans.

The characteristics and traits of EC2121951 are listed below.

TABLE 11

CHARACTERISTICS AND TRAITS

| | | | | | |
|---|---|---|---|---|---|
| Herbicide Transgene | | DAS-44406-6 | | | |
| Insect Transgene | | | | | |
| Other Transgene | | | | Relative Maturity | 2.800 |
| Sulfonylurea Tolerance | Y | | Seed Shape | Hypocotyl Color | |
| Metribuzin Tolerance | MET_S | | Seed Coat Luster | Plant Morphological | PGTIb |
| Aphid Gene | | | Peroxidase | Leaf Color | |
| % Protein @ 13% mst | | | Seed Size g/100 seeds | Leaf Shape Calculated | |
| % Oil @13% mst | | | Growth Habit | INDET | Leaf shape | |
| | | Plant Health | | | |

| | | | | | | | | | |
|---|---|---|---|---|---|---|---|---|---|
| | Phytophthora Gene | | | Rps1c | | Stem Canker Tolerance | | | |
| | Rust Gene | | | | | Chloride Sensitivity | CLMS | | |
| | SCN Res Source | | | 88788 | | RootKnot Nematode | | Sting Nematode | |
| R1 FI% | R2 FI% R3 FI% | R5 F1% R7 F1% | R9 FI% R14 FI% | Incognita | Arenaria | Javanica | Pratylenchus | | |
| | | | | | | | MI_U | | |

SCN = Soybean Cyst Nematode, RKN = Root Knot Nematode

Rps gene indicates the specific gene for resistance but if none are indicated then none are known to be present.

% Protein and % Oil are given at 13% moisture (standard moisture).

DAS-44406-6 indicates this variety carries the glyphosate, glufosinate, and 2,4-D tolerance cassette derived from event DAS-44406-6.

Seed shape: 1 = spherical; 2 = spherical-flattened; 3 = elongate; 4 = elongate-flattened Seed coat luster: 1 = dull; 2 = shiny Plant Morphological traits are listed in the order of flower, pubescence, pod color, and hilum. For flower, P—purple, W = white, and S = segregating (mixture of colors). For pubescence, G = gray, T = tawny, Lt = LT = light tawny, LBr = LB = light brown, and S = segregating (mixture of colors). For pod color, T = tan, B = brown, LBr = light brown, and S = segregating (mixture of colors). For hilum, G = gray, BR = Br = brown, MBr = medium brown, BF = Bf = buff, BL = Bl = black, IB = lb = imperfect black, Y = yellow, IY = Iy = imperfect yellow, S = segregating (mixture of colors).

Leaf Color: 1 = light green; 2 = medium green; 3 = dark green

Ratings are on a 1 to 9 scale with 1 being the best.

Sting Nematode is Pratylenchus.

Chloride sensitivity: CL = chloride, M = molecular marker results, X = segregating, S = susceptible marker allele present, R = resistant marker allele present.

CLMS = chloride sensitive and CLMR = chloride resistant

MI_S = susceptible, MI_R = resistant, MI_MR = mixed resistance. MI_U = unable to determine

TABLE 12

Agronomic and Disease Traits

| VHNO | Yield | Emerge | HrvstLod | GrnLod | MatDays | Height | Canopy | Branch | GrnStem | IDC |
|---|---|---|---|---|---|---|---|---|---|---|
| EC2121951 | 63.7 | 2.1 | 2.9 | 2.8 | 128.6 | 35.3 | 6.4 | 5.4 | 2.3 | 4.3 |
| GH2653XF | 59.2 | 3.1 | 1.6 | 1.8 | 126.8 | 30.0 | 5.1 | 4.7 | 3.0 | 4.6 |
| S28-E3 | 60.4 | 3.3 | 2.3 | 2.3 | 127.9 | 32.7 | 5.7 | 6.2 | 3.1 | 4.2 |
| NK25-C9XF | 62.9 | 3.1 | 2.6 | 3.2 | 125.5 | 35.1 | 6.3 | 4.9 | 2.5 | 4.1 |
| NK28-T3XF | 64.4 | 2.5 | 2.4 | 3.2 | 126.3 | 35.1 | 6.3 | 4.8 | 1.8 | 4.3 |
| NK29-Z4E3 | 62.3 | 2.8 | 2.1 | 2.3 | 129.6 | 32.6 | 6.0 | 6.6 | 3.1 | 3.6 |
| NK27-A7XF | 61.6 | 3.2 | 2.8 | 3.3 | 129.6 | 37.1 | 5.7 | 4.2 | 2.9 | 4.9 |
| Environments | 31.0 | 7.0 | 8.0 | 6.0 | 9.0 | 5.0 | 10.0 | 6.0 | 4.0 | 2.0 |
| Grand Mean | 62.0 | 2.5 | 2.4 | 2.8 | 126.0 | 34.1 | 5.7 | 5.3 | 2.4 | 3.8 |
| Check Mean | 61.5 | 2.9 | 2.3 | 2.7 | 126.6 | 34.0 | 5.7 | 5.2 | 2.5 | 4.1 |
| LSD (0.05) | 2.2 | 0.5 | 0.8 | 0.8 | 1.5 | 1.9 | 0.6 | 0.8 | 0.9 | 1.4 |

| VHNO | BSR_R | CR_R | FELS | PM_R | PRR | BP_R | RUSTR | SDS | SWM | TSP_R |
|---|---|---|---|---|---|---|---|---|---|---|
| EC2121951 | #N/A | #N/A | 4.5 | #N/A | 1.7 | #N/A | #N/A | 1.3 | 7.2 | #N/A |
| GH2653XF | #N/A | #N/A | 6.0 | #N/A | 2.7 | #N/A | #N/A | 1.8 | 5.4 | #N/A |
| S28-E3 | #N/A | #N/A | 3.5 | #N/A | 2.2 | #N/A | #N/A | 1.8 | 7.4 | #N/A |
| NK25-C9XF | #N/A | #N/A | 5.0 | #N/A | 2.0 | #N/A | #N/A | 1.8 | 6.5 | #N/A |
| NK28-T3XF | #N/A | #N/A | 5.5 | #N/A | 2.3 | #N/A | #N/A | 1.8 | 7.2 | #N/A |
| NK29-Z4E3 | #N/A | #N/A | 2.5 | #N/A | 2.3 | #N/A | #N/A | 1.3 | 6.6 | #N/A |

Not used.

TABLE 12-continued

| | | | | | | | | | | |
|---|---|---|---|---|---|---|---|---|---|---|
| | | | | Agronomic and Disease Traits | | | | | | |
| NK27-A7XF | #N/A | #N/A | 5.5 | #N/A | 2.3 | #N/A | #N/A | 1.5 | 7.2 | #N/A |
| Environments | #N/A | #N/A | 1.0 | #N/A | 1.0 | #N/A | #N/A | 2.0 | 1.0 | #N/A |
| Grand Mean | #N/A | #N/A | 4.1 | #N/A | 2.4 | #N/A | #N/A | 1.7 | 6.3 | #N/A |
| Check Mean | #N/A | #N/A | 4.3 | #N/A | 2.4 | #N/A | #N/A | 1.7 | 6.5 | #N/A |
| LSD (0.05) | #N/A | #N/A | 1.3 | #N/A | 0.0 | #N/A | #N/A | 1.6 | 0.0 | #N/A |

N/A = no data available

As the previous table indicates each of these lines has their own positive traits. Each of these lines is different from EC2121951. EC2121951 was tested by Syngenta Seeds, Inc. in Advanced Yield Trials in 2022. Data were collected for yield (bushels per acre), maturity date (95% mature pod color), harvest lodging (1=plant is upright to 9=plant is prostrate), and plant height in inches. EC2121951 is not significantly different for yield compared to NK25-C9XF, NK28-T3XF, NK29-Z4E3, and NK27-A7XF. EC2121951 has significantly higher yield than GH2653XF and S28-E3 (LSD 0.05-2.2 bu/ac). EC2121951 is not significantly different for harvest lodging compared to S28-E3, NK25-C9XF, NK28-T3XF, NK29-Z4E3, and NK27-A7XF. EC2121951 has significantly higher harvest lodging rating than GH2653XF (LSD 0.05=0.8). EC2121951 is not significantly different for maturity compared to S28-E3, NK29-Z4E3, and NK27-A7XF. EC2121951 is significantly later for maturity than GH2653XF, NK25-C9XF, and NK28-T3XF (LSD 0.05=1.5 days). EC2121951 is not significantly different for plant height than NK25-C9XF, NK28-T3XF, and NK27-A7XF. EC2121951 is significantly taller than GH2653XF, S28-E3, and NK29-Z4E3 (LSD 0.05=1.9 inches). EC2121951 is most similar to NK25-C9XF, NK28-Z4E3, and NK27-A7XF but can be differentiated by pubescence color. EC2121951 has gray pubescence and NK25-C9XF, NK28-Z4E3, and NK27-A7XF have light tawny pubescence. EC2121951 is most similar to S28-E3 and NK29-C9XF but can be differentiated by hilum color. EC2121951 has imperfect black hilum and S28-E3 and NK29-C9XF have buff hilum color. EC2121951 is most similar to GH2653XF but can be differentiated by plant height. EC2121951 has a plant height of 35.3 inches and GH2653XF has a significantly different plant height of 30.0 inches (LSD 0.05=1.9 inches).

EC2122916 is employed in a number of plot repetitions to establish trait characteristics.

EC2122916 is a novel soybean cultivar designated EC2122916 with high yield potential and tolerance to glyphosate, glufosinate, and 2,4-D herbicides. The invention relates to seeds of the cultivars EC2122916, plants of the cultivars EC2122916 and to methods for producing a soybean plant produced by crossing the soybean EC2122916 by itself or another soybean genotype.

EC2122916 is a Group 2 soybean cultivar. This variety has an RM of 2.600. To be sold commercially in the United States and Canada where Maturity Group 2 soybeans are grown. Specific areas where best adaption occurs includes Ontario, Illinois, Iowa, and Nebraska. The target for this variety is geographic regions that grow Group 2 maturity sulfonylurea, glyphosate, 2,4-D, and The characteristics and traits of EC2122916 are listed below.

TABLE 13

| CHARACTERISTICS AND TRAITS | | | | | |
|---|---|---|---|---|---|
| Herbicide Transgene | | | DAS-44406-6 | | |
| Insect Transgene | | | | | |
| Other Transgene | | | | Relative Maturity | 2.600 |
| Sulfonylurea Tolerance | N | | Seed Shape | Hypocotyl Color | |
| Metribuzin Tolerance | MET_S | | Seed Coat Luster | Plant Morphological | WGTBf |
| Aphid Gene | | | Peroxidase | Leaf Color | |
| % Protein @ 13% mst | | | Seed Size g/100 seeds | Leaf Shape Calculated | |
| % Oil @13% mst | | | Growth Habit　INDET | Leaf shape | |
| | | Plant Health | | | |
| Phytophthora Gene | | Rps1c | Stem Canker Tolerance | | |
| Rust Gene | | | Chloride Sensitivity　CLMS | | |
| SCN Res Source | | 88788 | RootKnot Nematode | Sting Nematode | |
| R1 FI%　R2 FI%　R3 FI% | R5 F1%　R7 F1% | R9 FI%　R14 FI% | Incognita　Arenaria　Javanica | Pratylenchus | |

SCN = Soybean Cyst Nematode, RKN = Root Knot Nematode

Rps gene indicates the specific gene for resistance but if none are indicated then none are known to be present.

% Protein and % Oil are given at 13% moisture (standard moisture).

DAS-44406-6 indicates this variety carries the glyphosate, glufosinate, and 2,4-D tolerance cassette derived from event DAS-44406-6.

Seed shape: 1 = spherical; 2 = spherical-flattened; 3 = elongate; 4 = elongate-flattened Seed coat luster: 1 = dull; 2 = shiny Plant Morphological traits are listed in the order of flower, pubescence, pod color, and hilum. For flower, P—purple, W = white, and S = segregating (mixture of colors). For pubescence, G = gray, T = tawny, Lt = LT = light tawny, LBr = LB = light brown, and S = segregating (mixture of colors). For pod color, T = tan, B = brown, LBr = light brown, and S = segregating (mixture of colors). For hilum, G = gray, BR = Br = brown, MBr = medium brown, BF = Bf = buff, BL = Bl = black, IB = Ib = imperfect black, Y = yellow, IY = Iy = imperfect yellow, S = segregating (mixture of colors).

Leaf Color: 1 = light green; 2 = medium green; 3 = dark green

Ratings are on a 1 to 9 scale with 1 being the best.

Sting Nematode is Pratylenchus

Chloride sensitivity: CL = chloride, M = molecular marker results, X = segregating, S = susceptible marker allele present, R = resistant marker allele present.

CLMS = chloride sensitive and CLMR = chloride resistant

ML_S = susceptible, ML_R = resistant, ML_MR = mixed resistance, ML_U = unable to determine

TABLE 14

| VHNO | Yield | Emerge | HrvstLod | GrnLod | MatDays | Height | Canopy | Branch | GrnStem | IDC |
|---|---|---|---|---|---|---|---|---|---|---|
| EC2122916 | 63.8 | 2.6 | 1.9 | 2.5 | 125.5 | 33.6 | 5.2 | 5.3 | 2.3 | 4.0 |
| GH2653XF | 59.2 | 3.1 | 1.6 | 1.8 | 126.8 | 30.0 | 5.1 | 4.7 | 3.0 | 4.6 |
| S28-E3 | 60.4 | 3.3 | 2.3 | 2.3 | 127.9 | 32.7 | 5.7 | 6.2 | 3.1 | 4.2 |
| NK25-C9XF | 62.9 | 3.1 | 2.6 | 3.2 | 125.5 | 35.1 | 6.3 | 4.9 | 2.5 | 4.1 |
| NK28-T3XF | 64.4 | 2.5 | 2.4 | 3.2 | 126.3 | 35.1 | 6.3 | 4.8 | 1.8 | 4.3 |
| NK29-Z4E3 | 62.3 | 2.8 | 2.1 | 2.3 | 129.6 | 32.6 | 6.0 | 6.6 | 3.1 | 3.6 |
| NK27-A7XF | 61.6 | 3.2 | 2.8 | 3.3 | 129.6 | 37.1 | 5.7 | 4.2 | 2.9 | 4.9 |
| Environments | 31.0 | 7.0 | 8.0 | 6.0 | 9.0 | 5.0 | 10.0 | 6.0 | 4.0 | 2.0 |
| Grand Mean | 62.0 | 2.5 | 2.4 | 2.8 | 126.0 | 34.1 | 5.7 | 5.3 | 2.4 | 3.8 |
| Check Mean | 61.5 | 2.9 | 2.3 | 2.7 | 126.6 | 34.0 | 5.7 | 5.2 | 2.5 | 4.1 |
| LSD (0.05) | 2.2 | 0.5 | 0.8 | 0.8 | 1.5 | 1.9 | 0.6 | 0.8 | 0.9 | 1.4 |

| VHNO | BSR_R | CR_R | FELS | PM_R | PRR | BP_R | RUSTR | SDS | SWM | TSP_R |
|---|---|---|---|---|---|---|---|---|---|---|
| EC2122916 | #N/A | #N/A | 4.0 | #N/A | 2.0 | #N/A | #N/A | 1.5 | 6.7 | #N/A |
| GH2653XF | #N/A | #N/A | 6.0 | #N/A | 2.7 | #N/A | #N/A | 1.8 | 5.4 | #N/A |
| S28-E3 | #N/A | #N/A | 3.5 | #N/A | 2.2 | #N/A | #N/A | 1.8 | 7.4 | #N/A |
| NK25-C9XF | #N/A | #N/A | 5.0 | #N/A | 2.0 | #N/A | #N/A | 1.8 | 6.5 | #N/A |
| NK28-T3XF | #N/A | #N/A | 5.5 | #N/A | 2.3 | #N/A | #N/A | 1.8 | 7.2 | #N/A |
| NK29-Z4E3 | #N/A | #N/A | 2.5 | #N/A | 2.3 | #N/A | #N/A | 1.3 | 6.6 | #N/A |
| NK27-A7XF | #N/A | #N/A | 5.5 | #N/A | 2.3 | #N/A | #N/A | 1.5 | 7.2 | #N/A |
| Environments | #N/A | #N/A | 1.0 | #N/A | 1.0 | #N/A | #N/A | 2.0 | 1.0 | #N/A |
| Grand Mean | #N/A | #N/A | 4.1 | #N/A | 2.4 | #N/A | #N/A | 1.7 | 6.3 | #N/A |
| Check Mean | #N/A | #N/A | 4.3 | #N/A | 2.4 | #N/A | #N/A | 1.7 | 6.5 | #N/A |
| LSD (0.05) | #N/A | #N/A | 1.3 | #N/A | 0.0 | #N/A | #N/A | 1.6 | 0.0 | #N/A |

N/A = no data available

As the previous table indicates each of these lines has their own positive traits. Each of these lines is different from EC2122916. EC2122916 was tested by Syngenta Seeds Inc. in Advanced Yield trials in 2022. Data were collected for yield (bushels per acre), maturity date (95% mature pod color), harvest lodging (1=plant is upright to 9=plant is prostrate), and plant height in inches. EC2122916 is not significantly different for yield compared to NK25-C9XF, NK28-T3XF, NK29-Z4E3, and NK27-A7XF. EC2122916 has significantly higher yield than GH2653XF and S28-E3 (LSD 0.05=2.2 bu/ac). EC2122916 is not significantly different for harvest lodging compared to GH2653XF, S28-E3, NK25-C9XF, NK28-T3XF, NK29-Z4E3, and NK27-A7XF (LSD 0.05=0.8). EC2122916 is not significantly different for maturity compared to GH2653XF, NK25-C9XF, NK28-T3XF. EC2122916 is significantly earlier than S28-E3, NK29-Z4E3, and NK27-A7XF (LSD 0.05=1.5 days). EC2122916 is not significantly different for plant height compared to S28-E3, NK25-C9XF, NK28-T3XF, and NK29-Z4E3. EC2122916 is significantly different for plant height than GH2653XF and NK27-A7XF (LSD 0.05=1.9 inches). EC2122916 is most similar to NK25-C9XF, NK28-T3XF, and NK27-A7XF but can be differentiated by pubescence color. EC2122916 has gray pubescence color and NK25-C9XF, NK28-T3XF, and NK27-A7XF have light tawny pubescence color. EC2122916 is most similar to GH2653XF but can be differentiated by pod color. EC2122916 has tan pod color and GH2653XF has brown pod color. EC2122916 is most similar to S28-E3 and NK29-Z4E3S but can be differentiated by resistance to Phytophthora sojae. EC2122916 has the Rps 1c resistance allele, S28-E3 has the Rps 1k resistance allele, and NK29-Z4E3 has the Rps 1k and Rps 3a resistance alleles.

EC2141386 is employed in a number of plot repetitions to establish trait characteristics.

EC2141386 is a novel soybean cultivar designated EC2141386 with high yield potential and tolerance to glyphosate, glufosinate, and dicamba herbicides. The invention relates to seeds of the cultivars EC2141386, plants of the cultivars EC2141386 and to methods for producing a soybean plant produced by crossing the soybean EC2141386 by itself or another soybean genotype.

EC2141386 is a Group 2 soybean cultivar. This variety has an RM of 2.800. To be sold commercially in the United States and Canada where Maturity Group 2 soybeans are grown. Specific areas where best adaption occurs includes Ontario, Iowa, Nebraska, and Illinois. The target for this variety is geographic regions that grow Group 2 maturity glyphosate, glufosinate, and dicamba tolerant soybeans.

The characteristics and traits of EC2141386 are listed below.

TABLE 15

| CHARACTERISTICS AND TRAITS | | | | | |
|---|---|---|---|---|---|
| Herbicide Transgene | | A5547-127; MON 87708; MON 89788 | | | |
| Insect Transgene | | | | | |
| Other Transgene | | | | Relative Maturity | 2.800 |
| Sulfonylurea Tolerance | N | | Seed Shape | Hypocotyl Color | |
| Metribuzin Tolerance | MET_R | | Seed Coat Luster | Plant Morphological | PGTBl |
| Aphid Gene | | | Peroxidase | Leaf Color | |
| % Protein @ 13% mst | | | Seed Size g/100 seeds | Leaf Shape Calculated | |
| % Oil @13% mst | | | Growth Habit | INDET | Leaf shape |

TABLE 15-continued

| CHARACTERISTICS AND TRAITS |
| --- |

| Plant Health |
| --- |

| | Phytophthora Gene Rust Gene SCN Res Source | | | | | Rps1c 88788 | | Stem Canker Tolerance Chloride Sensitivity CLMS RootKnot Nematode | | | Sting Nematode |
| R1 FI% | R2 FI% | R3 FI% | R5 F1% | R7 F1% | R9 FI% | R14 FI% | Incognita | Arenaria | Javanica | Pratylenchus |
| --- | --- | --- | --- | --- | --- | --- | --- | --- | --- | --- |

SCN = Soybean Cyst Nematode, RKN = Root Knot Nematode
Rps gene indicates the specific gene for resistance but if none are indicated then none are known to be present.
% Protein and % Oil are given at 13% moisture (standard moisture).
A5547-127 indicates this variety carries the glufosinate tolerance transgene derived from event A5547-127.
MON89788 indicates this variety carries the glyphosate tolerance transgene derived from event MON 89788.
MON87708 indicates this variety carries the dicamba tolerance transgene derived from event MON 87708.
Seed shape: 1 = spherical; 2 = spherical-flattened; 3 = elongate; 4 = elongate-flattened
Seed coat luster: 1 = dull; 2 = shiny
Plant Morphological traits are listed in the order of flower, pubescence, pod color, and hilum. For flower, P—purple, W = white, and S = segregating (mixture of colors). For pubescence, G = gray, T = tawny, Lt = LT = light tawny, LBr = LB = light brown, and S = segregating (mixture of colors). For pod color, T = tan, B = brown, LBr = light brown, and S = segregating (mixture of colors). For hilum, G = gray, BR = Br = brown, MBr = medium brown, BF = Bf = buff, BL = Bl = black, IB = Ib = imperfect black, Y = yellow, IY = Iy = imperfect yellow, S = segregating (mixture of colors).
Leaf Color: 1 = light green; 2 = medium green; 3 = dark green
Ratings are on a 1 to 9 scale with 1 being the best.
Sting Nematode is Pratylenchus
Chloride sensitivity: CL = chloride, M = molecular marker results, X = segregating, S = susceptible marker allele present, R = resistant marker allele present.
CLMS = chloride sensitive and CLMR = chloride resistant
ML_S = susceptible, ML_R = resistant, ML_MR = mixed resistance, ML_U = unable to determine

TABLE 16

| Agronomic and Disease Traits | | | | | | | | | | |
| --- | --- | --- | --- | --- | --- | --- | --- | --- | --- | --- |
| VHNO | Yield | Emerge | HrvstLod | GrnLod | MatDays | Height | Canopy | Branch | GrnStem | IDC |
| GH2653XF | 59.2 | 3.1 | 1.6 | 1.8 | 126.8 | 30.0 | 5.1 | 4.7 | 3.0 | 4.6 |
| S28-E3 | 60.4 | 3.3 | 2.3 | 2.3 | 127.9 | 32.7 | 5.7 | 6.2 | 3.1 | 4.2 |
| EC2141386 | 65.2 | 2.5 | 2.3 | 3.0 | 129.2 | 38.6 | 5.3 | 5.1 | 3.5 | 3.7 |
| NK25-C9XF | 62.9 | 3.1 | 2.6 | 3.2 | 125.5 | 35.1 | 6.3 | 4.9 | 2.5 | 4.1 |
| NK28-T3XF | 64.4 | 2.5 | 2.4 | 3.2 | 126.3 | 35.1 | 6.3 | 4.8 | 1.8 | 4.3 |
| NK29-Z4E3 | 62.3 | 2.8 | 2.1 | 2.3 | 129.6 | 32.6 | 6.0 | 6.6 | 3.1 | 3.6 |
| NK27-A7XF | 61.6 | 3.2 | 2.8 | 3.3 | 129.6 | 37.1 | 5.7 | 4.2 | 2.9 | 4.9 |
| Environments | 31.0 | 7.0 | 8.0 | 6.0 | 9.0 | 5.0 | 10.0 | 6.0 | 4.0 | 2.0 |
| Grand Mean | 62.0 | 2.5 | 2.4 | 2.8 | 126.0 | 34.1 | 5.7 | 5.3 | 2.4 | 3.8 |
| Check Mean | 61.5 | 2.9 | 2.3 | 2.7 | 126.6 | 34.0 | 5.7 | 5.2 | 2.5 | 4.1 |
| LSD (0.05) | 2.2 | 0.5 | 0.8 | 0.8 | 1.5 | 1.9 | 0.6 | 0.8 | 0.9 | 1.4 |

| VHNO | BSR_R | CR_R | FELS | PM_R | PRR | BP_R | RUSTR | SDS | SWM | TSP_R |
| --- | --- | --- | --- | --- | --- | --- | --- | --- | --- | --- |
| GH2653XF | #N/A | #N/A | 6.0 | #N/A | 2.7 | #N/A | #N/A | 1.8 | 5.4 | #N/A |
| S28-E3 | #N/A | #N/A | 3.5 | #N/A | 2.2 | #N/A | #N/A | 1.8 | 7.4 | #N/A |
| EC2141386 | #N/A | #N/A | 4.5 | #N/A | 2.0 | #N/A | #N/A | 1.3 | 4.5 | #N/A |
| NK25-C9XF | #N/A | #N/A | 5.0 | #N/A | 2.0 | #N/A | #N/A | 1.8 | 6.5 | #N/A |
| NK28-T3XF | #N/A | #N/A | 5.5 | #N/A | 2.3 | #N/A | #N/A | 1.8 | 7.2 | #N/A |
| NK29-Z4E3 | #N/A | #N/A | 2.5 | #N/A | 2.3 | #N/A | #N/A | 1.3 | 6.6 | #N/A |
| NK27-A7XF | #N/A | #N/A | 5.5 | #N/A | 2.3 | #N/A | #N/A | 1.5 | 7.2 | #N/A |
| Environments | #N/A | #N/A | 1.0 | #N/A | 1.0 | #N/A | #N/A | 2.0 | 1.0 | #N/A |
| Grand Mean | #N/A | #N/A | 4.1 | #N/A | 2.4 | #N/A | #N/A | 1.7 | 6.3 | #N/A |
| Check Mean | #N/A | #N/A | 4.3 | #N/A | 2.4 | #N/A | #N/A | 1.7 | 6.5 | #N/A |
| LSD (0.05) | #N/A | #N/A | 1.3 | #N/A | 0.0 | #N/A | #N/A | 1.6 | 0.0 | #N/A |

N/A = no data available

As the previous table indicates each of these lines has their own positive traits. Each of these lines is different from EC2141386. EC2141386 is a glyphosate, glufosinate, and dicamba tolerant soybean developed through conventional breeding methods by Syngenta Seeds, Inc. It was a F4 plant selection from a single cross of CE1610822 of CG18000149. EC2141386 was tested by Syngenta Seeds, Inc. in Advanced yield trials in 2022. Data were collected for yield (bushels per acre), maturity date (95% mature pod color), harvest lodging (1=plant is upright to 9=plant is prostrate), and plant height in inches. EC2141386 is not significantly different for yield compared to NK25-C9XF and NK28-T3XF. EC2141386 has significantly higher yield than GH2653XF, S28-E3, NK29-Z4E3, and NK27-A7XF (LSD 0.05=2.2 bu/ac). EC2141386 is not significantly different for harvest lodging compared to GH2653XF, S28-E3, NK25-C9XF, NK28-T3XF, NK29-Z4E3, and NK27-A7XF (LSD 0.05=0.8). EC2141386 is not significantly different for days to maturity compared to S28-E3, NK29-Z4E3, and NK27-A7XF. EC2141386 is significantly later than GH2653XF, NK25-C9XF, and NK28-T3XF (LSD 0.05=1.5 days). EC2141386 is not significantly different for plant height compared to NK27-A7XF. EC2141386 is significantly taller than GH2653XF, S28-E3, NK25-C9XF, NK28-T3XF, and NK29-Z4E3 (LSD 1.9 inches). EC2141386 is most similar to GH2653XF, S28-E3, and NK29-Z4E3 but can be differentiated by pubescence color. EC2141386 has light tawny pubescence color and GH2653XF, S28-E3, and NK29-Z4E3 have gray pubescence color. EC2141386 is most similar to NK25-C9XF and NK27-A7XF but can be differentiated by pod color. EC2141386 has tan pod color and NK25-C9XF and NK27-A7XF have brown pod color. EC2141386 is most similar to NK28-T3XF but can be differentiated by resistance to *Phytophthora sojae.* EC2141386 has the Rps 1c allele resistance to *Phytophthora sojae* and NK28-T3XF does not.

Accordingly, the present invention has been described with some degree of particularity directed to the preferred embodiment of the present invention. It should be appreciated, though that the present invention is defined by the following claims construed in light of the prior art so that modifications or changes may be made to the preferred embodiment of the present invention without departing from the inventive concepts contained herein.

What is claimed:

1. A plant, a plant part, or a seed of soybean line EC2020188, wherein a representative sample of seed of said soybean line EC2020188 has been deposited under ATCC Accession Number PTA-127457.

2. A cell of the plant of claim 1.

3. A soybean plant obtained by transforming the soybean plant of claim 1.

4. A seed of the soybean plant according to claim 3.

5. A method for producing a soybean seed, said method comprising crossing soybean plants and harvesting the resultant soybean seed, wherein at least one soybean plant is the soybean plant of claim 1.

6. The method of claim 5, wherein the method further comprises:

(a) crossing a plant grown from said resultant soybean seed with itself or a different soybean plant to produce a seed of a progeny plant of a subsequent generation;

(b) growing a progeny plant of a subsequent generation from said seed of a progeny plant of a subsequent generation and crossing the progeny plant of a subsequent generation with itself or a second plant to produce a progeny plant of a further subsequent generation; and (c) repeating steps (a) and (b) using said progeny plant of a further subsequent generation from step (b) in place of the plant grown from said resultant soybean seed in step (a), wherein steps (a) and (b) are repeated with sufficient inbreeding to produce an inbred soybean plant derived from soybean line EC2020188, wherein a representative sample of seed of said soybean line EC2020188 has been deposited under ATCC Accession Number PTA-127457.

7. An F1 soybean seed produced by the method of claim 5.

8. An F1 soybean seed produced by the method of claim 5 wherein at least one of the soybean plants carries a heritable transgenic event.

9. An F1 soybean plant, or part thereof, produced by growing said seed of claim 7.

10. A method for developing a second soybean plant through plant breeding, said method comprising applying plant breeding to said soybean plant, or parts thereof according to claim 1, wherein said plant breeding results in development of said second soybean plant.

11. A method of producing a soybean plant comprising a desired trait, the method comprising introducing a single transgene or locus conferring the desired trait into the soybean plant EC2020188 of claim 1, wherein a representative sample of seed of said soybean line EC2020188 has been deposited under ATCC Accession Number PTA-127457.

12. The method of claim 11, wherein the desired trait is selected from the group consisting of male sterility, herbicide tolerance, insect resistance, nematode resistance, pest resistance, disease resistance, fungal resistance, modified fatty acid metabolism, modified carbohydrate metabolism, drought tolerance, abiotic stress tolerance, a site-specific recombination site, and modified nutrient deficiency tolerances.

13. A plant produced by the method of claim 11, wherein the plant has said desired trait and all of the morphological and physiological characteristics of soybean line EC2020188 other than those characteristics altered by said transgene or locus when grown in the same location and in the same environment, wherein a representative sample of seed of said soybean line EC2020188 has been deposited under ATCC Accession Number PTA-127457.

14. A method of introducing a single locus conversion into a soybean plant, wherein the method comprises:

(a) crossing the EC2020188 plant of claim 1 with a plant of another soybean line that comprises the single locus to produce F1 progeny plants;

(b) selecting one or more F1 progeny plants from step (a) to produce selected progeny plants;

(c) selfing selected progeny plants of step (b) or crossing the selected progeny plants of step (b) with the EC2020188 plants to produce later generation selected progeny plants;

(d) crossing or further selecting for later generation selected progeny plants that have the single locus and physiological and morphological characteristics of soybean line EC2020188 to produce selected next later generation progeny plants; and optionally (e) repeating crossing or selection of later generation progeny plants to produce progeny plants that comprise the single locus and all of the physiological and morphological characteristics of said single locus and of soybean line EC2020188 when grown in the same location and in the same environment, wherein a representative sample of seed of said soybean line EC2020188 has been deposited under ATCC Accession Number PTA-127457.

15. A plant produced by the method of claim 14 or a selfed progeny thereof, wherein the plant or selfed progeny thereof comprises said single locus and otherwise comprises essentially all of the physiological and morphological characteristics of soybean line EC2020188, wherein a representative sample of seed of said soybean line EC2020188 has been deposited under ATCC Accession Number PTA-127457.

16. A method of producing a commodity plant product, said method comprising obtaining the plant of claim 1 or a part thereof and producing said commodity plant product comprising protein concentrate, protein isolate, soybean hulls, meal, flour, or oil from said plant or said part thereof.

17. A seed that produces the plant of claim 13.

18. A method comprising isolating nucleic acids from a plant, a plant part, or a seed of soybean line EC2020188 analyzing said nucleic acids to produce data, and recording the data for soybean line EC2020188, wherein a representative sample of seed of said soybean line EC2020188 has been deposited under ATCC Accession Number PTA-127457.

19. The method of claim 18, wherein the data is recorded on a computer readable medium.

20. The method of claim 18, further comprising using the data for crossing, selection, or advancement decisions in a breeding program.

\* \* \* \* \*